United States Patent
Guney et al.

(10) Patent No.: US 11,826,511 B2
(45) Date of Patent: Nov. 28, 2023

(54) TEXTILE CONDUIT WITH WINDOWS

(71) Applicant: ResMed Pty Ltd, Bella Vista (AU)

(72) Inventors: Memduh Guney, Sydney (AU); Michiel Kooij, Sydney (AU); Jeremy McManus, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/773,075

(22) PCT Filed: Oct. 30, 2020

(86) PCT No.: PCT/AU2020/051179
§ 371 (c)(1),
(2) Date: Apr. 29, 2022

(87) PCT Pub. No.: WO2021/081595
PCT Pub. Date: May 6, 2021

(65) Prior Publication Data
US 2022/0401684 A1    Dec. 22, 2022

(30) Foreign Application Priority Data
Oct. 31, 2019  (AU) ................................ 2019904118

(51) Int. Cl.
*A61M 16/06*  (2006.01)
*A61M 16/08*  (2006.01)
*A61M 16/20*  (2006.01)

(52) U.S. Cl.
CPC .... *A61M 16/0683* (2013.01); *A61M 16/0616* (2014.02); *A61M 16/0666* (2013.01);
(Continued)

(58) Field of Classification Search
CPC .............. A61M 16/06; A61M 16/0611; A61M 16/0616; A61M 16/0622; A61M 16/0633;
(Continued)

(56) References Cited

U.S. PATENT DOCUMENTS 916,567 A * 3/1909 Leonard ................ A61M 16/18
285/261
4,782,832 A  11/1988 Trimble et al.
(Continued)

FOREIGN PATENT DOCUMENTS

WO    WO 98/004310 A1    2/1998
WO    WO 98/034665 A1    8/1998
(Continued)

OTHER PUBLICATIONS

"*Respiratory Physiology*", by John B. West, Lippincott Williams & Wilkins, $9^{th}$ edition published 2012 (8 pages).
(Continued)

*Primary Examiner* — Annette Dixon
(74) *Attorney, Agent, or Firm* — Nixon & Vanderhye P.C.

(57) ABSTRACT

A patient interface a positioning and stabilising structure, which includes a gas delivery tube with a tube wall that has an interior passage for flow of pressurized air. A portion of the tube wall includes a patient contacting portion and a non-patient contacting portion. The patient contacting portion includes a layer of textile material or foam material configured to lie against the patient's head. At least a section of the non-patient contacting portion includes of a transparent and/or translucent material. The layer of textile material or foam material is bonded to the transparent and/or translucent material so that the tube wall is formed as a one piece construction. A plane extends generally transverse to longitudinal axis contains both (1) the textile material or foam material and (2) the transparent and/or translucent material, so that the patient may view the interior passage along a transverse axis extending through the plane.

30 Claims, 15 Drawing Sheets

(52) U.S. Cl.
CPC .... *A61M 16/0816* (2013.01); *A61M 16/0875* (2013.01); *A61M 16/20* (2013.01); *A61M 2205/02* (2013.01)

(58) Field of Classification Search
CPC .......... A61M 16/0666; A61M 16/0683; A61M 16/0694; A61M 16/08; A61M 16/0825; A61M 16/0833; A61M 16/0875; A61M 16/1045; A61M 16/18; A61M 16/20; A61M 2205/02; A61M 2205/0238; A61M 2205/273; A61M 2205/583; A61M 2205/588; A61M 2205/59; A61M 2209/06; A61M 2209/082; A61M 2209/088; A61M 2210/0618; A61M 2210/0625; A61M 39/08; A62B 18/025; A62B 18/084; A62B 7/00; F16L 11/111
See application file for complete search history.

(56) References Cited

U.S. PATENT DOCUMENTS

| | | | |
|---|---|---|---|
| 4,944,310 | A | 7/1990 | Sullivan |
| 5,584,286 | A * | 12/1996 | Kippax .................... A62B 7/00 128/200.24 |
| 5,687,715 | A | 11/1997 | Landis |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 10,029,062 | B2 | 7/2018 | Kwok et al. |
| 2007/0246043 | A1 | 10/2007 | Kwok et al. |
| 2008/0047560 | A1 * | 2/2008 | Veliss ................ A61M 16/0611 128/207.11 |
| 2008/0060649 | A1 * | 3/2008 | Veliss .................. A62B 18/025 128/207.18 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0247619 | A1 * | 10/2011 | Formica ................ F16L 11/111 128/205.25 |
| 2018/0250482 | A1 | 9/2018 | Barlow et al. |
| 2019/0175851 | A1 | 6/2019 | Barlow et al. |
| 2019/0209799 | A1 | 7/2019 | Ovzinsky et al. |
| 2019/0269870 | A1 | 9/2019 | Kwok et al. |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2020/079617 A1 | 4/2020 |

OTHER PUBLICATIONS

International Search Report dated Dec. 22, 2020 issued in International Application No. PCT/AU2020/051179 (9 pages).
Written Opinion of the International Searching Authority dated Dec. 22, 2020 issued in International Application No. PCT/AU2020/051179 (6 pages).
International Preliminary Report on Patentability dated Oct. 11, 2021 issued in International Application No. PCT/AU2020/051179 (24 pages).

* cited by examiner

TEXTILE CONDUIT WITH WINDOWS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

CROSS-REFERENCE TO RELATED APPLICATION

This application is the U.S. national phase of International Application No. PCT/AU2020/051179 filed Oct. 30, 2020 which designated the U.S. and claims priority to AU 2019904118 filed Oct. 31, 2019, the entire contents of each of which are hereby incorporated by reference.

BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchairbound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; and WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the structure to position and stabilise the seal-forming portion of the patient interface to the appropriate part of the patient's face, also referred to as "headgear". This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to a tube in the patient interface through a port positioned in use on top of the patient's head.

The Philips DreamWear™ mask includes such headgear tubing. The length of the DreamWear™ headgear tubes cannot be adjusted. Consequently, the DreamWear™ headgear is supplied in three different sizes to cater for different sized patient faces. Providing a greater number of different sizes may increase the complexity and cost to manufacture the headgear and may result in larger packaging. Additionally, a supply of discretely sized masks may limit the extent to which differently sized patient heads can be accommodated. There may be a greater chance of some patients being unable to achieve what they consider a "perfect" fit if forced to choose between discrete sizes that are not adjustable in length.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One aspect of the present technology comprises a patient interface for delivery of a supply of pressurised breathable gas to an entrance of a patient's airways.

Another aspect of the present technology is directed to a patient interface that includes a seal-forming structure constructed and arranged to form a seal with a region of the patient's face surrounding an entrance to the patient's airways for sealed delivery of a flow of pressurized air at a therapeutic pressure of at least 6 cmH2O above ambient air pressure throughout the patient's respiratory cycle in use; a plenum chamber pressurisable to the therapeutic pressure of at least 6 cmH2O above ambient air pressure; and positioning and stabilising structure to provide a force to hold a seal-forming structure in a therapeutically effective position on a patient's head.

Another aspect of the present technology is directed to a patient interface that includes: a plenum chamber; a seal-forming structure; a vent structure; and a positioning and stabilising structure to provide a force to hold the seal-forming structure in a therapeutically effective position on a patient's head, the positioning and stabilising structure including at least one gas delivery tube to receive the flow of air from a connection port and to deliver the flow of air to the entrance of the patient's airways via the seal-forming structure, the gas delivery tube being constructed and arranged to contact, in use, at least a region of the patient's head superior to an otobasion superior of the patient's head.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure, the tube wall comprising:
  a patient contacting portion comprising a first outer layer comprising a textile material or foam material configured to lie against the patient's head in use; and
  a non-patient contacting portion comprising a second outer layer comprising a textile material or foam material on an opposing side of the gas delivery tube to the first outer layer.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:
  at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure, wherein at least a portion of the tube wall comprises:
    a patient contacting portion comprising a layer of textile material or foam material configured to lie against the patient's head in use; and
    a non-patient contacting portion, wherein at least a section of the non-patient contacting portion is comprised of a transparent material.

According to one aspect of the present technology, patient interface comprising:
  a seal-forming structure constructed and arranged to form a seal with a region of the patient's face surrounding an entrance to the patient's airways for sealed delivery of a flow of pressurized air at a therapeutic pressure of at least 6 cmH$_2$O above ambient air pressure throughout the patient's respiratory cycle in use;
  a plenum chamber pressurisable to the therapeutic pressure of at least 6 cmH$_2$O above ambient air pressure; and
  a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use, the positioning and stabilising structure comprising:
    at least one gas delivery tube coupled to the plenum chamber and configured to receive the flow of pressurized air from a connection port on top of the patient's head and to deliver the flow of pressurized air to the entrance of the patient's airways via the plenum chamber, the at least one gas delivery tube being constructed and arranged to contact, in use, at least a region of the patient's head superior to an otobasion superior of the patient's head, the at least one gas delivery tube comprising a tube wall having an interior passage for flow of pressurized air along a longitudinal axis of the tube to the seal-forming structure, wherein at least a portion of the tube wall comprises:
      a patient contacting portion comprising a layer of textile material or foam material configured to lie against the patient's head in use; and
      a non-patient contacting portion, wherein at least a section of the non-patient contacting portion is comprised of a transparent and/or translucent material to allow viewing of the passage from outside;
      wherein the layer of textile material is bonded to the transparent and/or translucent material so that the tube wall is formed as a one piece construction; and
      wherein a plane extending generally transverse to longitudinal axis contains both (1) the textile material or foam material and (2) the transparent and/or translucent material, so that the patient may view the passage along a transverse axis extending through the plane.

In examples, the patient contacting portion may comprise more than one layer. In these examples, the patient contacting portion may comprise an outer layer of textile material or foam material configured to lie against the patient's head in use, and at least a first inner layer of a thermoplastic material forming at least a portion of an air path within the at least one gas delivery tube. The first inner layer is bonded to the outer layer.

In examples, the patient contacting portion comprises a single layer of textile material or foam material. In these examples, (a) a material property of the textile material or that foam material is that it is impermeable; and/or (b) the textile material or foam material is coated with an impermeable substance along at least one surface, which forms an inner surface of the at least one gas delivery tube configured to be contacted by the flow of pressurized gas.

In examples, the textile material or foam material may comprise: (a) a blend of polyamide, for example, a nylon, polyester and/or spandex; (b) a blend of polyamide, for example, a nylon, polyester and/or spandex and one or more laminate coats of silicone. In this example, each laminate coat of silicone may be between 5 to 75 microns thick. In a further example, each laminate coat of silicone may be between 20 to 30 microns thick, preferably 25 microns thick.

In examples, the patient contacting portion may comprise a section of transparent and/or translucent material, wherein a portion of the section of transparent and/or translucent material is configured to receive the textile material or foam material. In these examples, the section of transparent and/or translucent material of the non-patient contacting portion may comprise an adhesive layer configured to be bonded to the textile material or foam material.

In examples, the non-patient contacting portion may comprise a section configured to receive the section of transparent and/or translucent material. In examples of this technology, the textile material or foam material of the non-patient contacting portion may comprise: (a) an adhesive layer configured to be bonded to the section of transparent and/or translucent material; or (b) a layer of hook and loop material configured to co-operatively engage with a complementary layer of hook and loop material bonded to the section of transparent and/or translucent material.

In examples, one of the patient contacting portion or non-patient contacting portion is configured to receive: (a) an adhesive layer to which the other of the patient contacting portion or non-patient contacting portion may be bonded; or (b) a layer of hook and loop material configured to cooperatively engage with a complementary layer of hook and loop material bonded to the other of the patient contacting portion or non-patient contacting portion.

In examples, the non-patient contacting portion may comprise two more layers. In these examples, the non-patient contacting portion may comprise an outer layer of transparent and/or translucent material and at least a first inner layer of a thermoplastic material defining at least a portion of an air path within the at least one gas delivery tube.

In examples, at least a portion of the section of transparent and/or translucent material: (a) is configured as a rigidising element; and/or (b) comprises a concertina section; and/or (c) comprises a series of corrugations. In this example, (a) a textile material or a foam material is overmolded onto the concertina section; (b) the textile material or the foam material is on the patient contacting portion, and configured to contact the patient; and/or (c) the textile material or the foam material is on the non-patient contacting portion.

In one example of this technology, the section of transparent and/or translucent material may run substantially the length of the at least one gas delivery tube. In another example of this technology, the section of transparent and/or translucent material may run a portion of the length of the at least one gas delivery tube. In yet another example of this technology, the transparent and/or translucent material may be arranged in discrete sections, each section separated by a section of non-transparent and/or translucent material, such as textile material or foam material, along the length of the at least one gas delivery tube.

In one example, the patient contacting portion and the non-patient contacting portion may each be elongate and each comprise a side that in use faces anteriorly (the anterior side of the at least one gas delivery tube in use) and posteriorly (the posterior side of the at least one gas delivery tube in use) respectively. The respective anterior and posterior sides of the patient contacting portion and the non-patient contacting portion are joined along the length of the at least one gas delivery tube. In this example, at least one or both of the anterior side and posterior side of the non-patient contacting side is comprised of the transparent and/or translucent material.

In this example, the anterior side of the non-patient contacting portion may have a different rigidity to the posterior side; (a) the anterior side of the non-patient contacting portion may comprise a greater rigidity than the posterior side of the non-patient contacting portion; (b) the anterior side of the non-patient contacting portion and/or the posterior side of the non-patient contacting portion may have a rigidity which varies along the length of the at least one gas delivery tube; (c) the rigidity of the anterior side of the non-patient contacting portion and/or the posterior side of the non-patient contacting portion may be greater at an inferior portion of the at least one gas delivery tube than at a superior portion of the at least one gas delivery tube.

In examples, the section of transparent and/or translucent material of the second outer layer may be formed from an elastomer, wherein the elastomer is one or more of a) silicone; b) thermoplastic elastomer (TPE); or c) thermoplastic polyurethane (TPU).

In further examples: (a) the patient contacting portion and/or the non-patient contacting portion may be thermoformed to shape; (b) the at least one gas delivery tube may comprise a substantially D-shaped cross section; (c) the at least one gas delivery tube may comprise a substantially rectangular cross section with two or more rounded corners; (d) the at least one gas delivery tube may vary in width from 34 mm to 18 mm along a length of the at least one gas delivery tube; (e) the at least one gas delivery tube may vary in height from 8 mm to 6 mm along a length of the at least one gas delivery tube; and/or (f) the non-patient contacting portion comprises a transparent material only. In these examples, (i) the D-shaped cross section includes a substantially flat surface and an arcuate surface, the flat surface forming the patient contacting portion and the arcuate surface forming the non-patient contacting portion; (ii) the arcuate surface includes a first section and a second section, the first section being constructed from the transparent and/or translucent material, and the second section being constructed from the textile material or foam material; and/or (iii) the first section is directly coupled to the flat surface, and the second section is disposed opposite to the flat surface.

In examples, method of manufacturing comprises positioning the textile material or the foam material in a mold; introducing the transparent and/or translucent material into the mold; bonding the transparent and/or translucent material to the textile material and/or the foam material in order to form the at least one gas delivery tube; and connecting the at least one gas delivery tube to the plenum chamber and/or the seal forming structure. In these examples, (a) the mold includes a semi-circular protrusion and the transparent and/or translucent material flowing around the semi-circular protrusion and creating a semi-circular recess along the hollow interior; and/or (b) the semi-circular protrusion directs the transparent and/or translucent material toward the textile material or the foam material in order to allow bonding between the transparent and/or translucent material and the textile material or the foam material prior to forming the non-patient contacting portion.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the at least one gas delivery tube being constructed and arranged to contact, in use, at least a region of the patient's head superior to an otobasion superior of the patient's head, the at least one gas delivery tube comprising a tube wall defining a hollow interior through which air is able to flow to the seal-forming structure, and wherein at least a portion of the tube wall comprises:

a patient contacting portion comprising an outer layer of textile material or foam material configured to lie against the patient's head in use; and a non-patient contacting portion comprising at least a section of transparent material;

a rigidising element, wherein the rigidising element is a section of the transparent material. In one example, the transparent material of the non-patient contacting portion may be an elastomer, wherein the elastomer is one or more of a) silicone; b) thermoplastic elastomer (TPE); or c) thermoplastic polyurethane (TPU).

In one example of this technology, the transparent section may run substantially the length of the at least one gas delivery tube. In another example of this technology, the transparent section runs a portion of the length of the at least one gas delivery tube. In yet another example of this technology, the transparent section is arranged at regular intervals along the length of the at least one gas delivery tube.

In one example, the patient contacting portion and the non-patient contacting portion may each be elongate and each comprise a side that in use faces anteriorly (the anterior side of the at least one gas delivery tube in use) and posteriorly (the posterior side of the at least one gas delivery tube in use) respectively. The respective anterior and posterior sides of the patient contacting portion and the non-patient contacting portion are joined along the length of the at least one gas delivery tube. In this example, at least one or both of the anterior side and posterior side of the non-patient contacting side is comprised of the transparent material.

In one example, the rigidising element may be provided to one of the anterior edge and the posterior sides of the at least one gas delivery tube.

In this example, the anterior side of the at least one gas delivery tube may have a different rigidity to the posterior side of the at least one gas delivery tube; (a) the anterior side of the at least one gas delivery tube may comprise a greater rigidity than the posterior side of the at least one gas delivery tube; (b) the anterior side of the at least one gas delivery tube and/or the posterior side of the at least one gas delivery tube may have a rigidity which varies along the length of the at least one gas delivery tube; (c) the rigidity of the anterior side of the at least one gas delivery tube and/or the posterior side of the at least one gas delivery tube may be greater at an inferior portion of the at least one gas delivery tube than at a superior portion of the at least one gas delivery tube.

In examples, the rigidising element is formed by: a) the thickness of the section of transparent material is greater at a first portion of the at least one gas delivery tube relative to a second portion of the at least one gas delivery tube; b) the width of the section of transparent material is greater at a first portion of the at least one gas delivery tube relative to a second portion of the at least one gas delivery tube. In these examples, the first portion is the inferior portion of the at least one gas delivery tube and the second portion is the superior portion of the at least one gas delivery tube. In other examples, the first portion is the superior portion of the at least one gas delivery tube and the second portion is the inferior portion of the at least one gas delivery tube. In further examples, the first portion is the anterior side of the at least one gas delivery tube and the second portion is the posterior side of the at least one gas delivery tube or the first portion is the posterior portion of the at least one gas delivery tube and the second portion is the anterior portion of the at least one gas delivery tube.

In examples, the non-patient contacting side includes an anterior facing side and a posterior facing side, configured to face in an anterior direction and a posterior direction respectively, in use. In these examples, (a) the anterior facing side and the posterior facing side are each constructed from the transparent and/or translucent material; and/or (b) the transverse axis extends generally from the anterior direction to the posterior direction includes only the transparent and/or translucent material.

In an example, the at least one gas delivery tube is selectively coupled to the plenum chamber, and is configured to be removed in order to allow the patient to clean within the tube.

According to another aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the at least one gas delivery tube being constructed and arranged to contact, in use, at least a region of the patient's head superior to an otobasion superior of the patient's head, the at least one gas delivery tube comprising a tube wall defining a hollow interior through which air is able to flow to the seal-forming structure, the at least one gas delivery tube comprising, in use:

a superior tube portion and an inferior tube portion, wherein the tube wall of the superior tube portion comprises a patient contacting portion comprising an elastomer and a non-patient contacting portion comprising an elastomer, and wherein the tube wall of the inferior tube portion comprises a patient contacting portion comprising a first layer of textile material or foam material configured to lie against the patient's head in use, and a non-patient contacting portion comprising a second outer layer, wherein at least a portion of the second outer layer is comprised of a transparent material.

In examples, the first layer of textile material is a fabric material of one or more of a) nylon; b) polyester c) spandex.

In examples, the first layer of textile material is a) bonded to the second outer layer by adhesive; b) bonded to the second outer layer by hook and loop material.

In one example, the first layer of textile material is also provided to the superior tube portion.

In one example, the transparent material of the second outer layer may be an elastomer, wherein the elastomer is one or more of a) silicone; b) thermoplastic elastomer (TPE); or c) thermoplastic polyurethane (TPU).

According to one aspect of the present technology, there is provided a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

the positioning and stabilising structure according to any one of the above aspects; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered.

Another aspect of certain forms of the present technology is a system for treating a respiratory disorder comprising a patient interface according to any one or more of the other aspects of the present technology, an air circuit and a source of air at positive pressure.

According to one aspect of the present technology there is provided a method of manufacturing a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure, wherein at least a portion of the tube wall comprises:

a patient contacting portion comprising an outer layer of textile material or foam material configured to lie against the patient's head in use; and a non-patient contacting portion, wherein at least a section of the non-patient contacting portion is comprised of a transparent material.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment.

According to one aspect of the present technology, a patient interface comprising:

a seal-forming structure constructed and arranged to form a seal with a region of the patient's face surrounding an entrance to the patient's airways for sealed delivery of a flow of pressurized air at a therapeutic pressure of at least 6 cmH$_2$O above ambient air pressure throughout the patient's respiratory cycle in use;

a plenum chamber pressurisable to the therapeutic pressure of at least 6 cmH2O above ambient air pressure; and a positioning and stabilising structure to provide a force to hold a seal-forming structure in a therapeutically effective position on a patient's head.

According to one aspect of the present technology, at least one gas delivery tube coupled to the plenum chamber and configured to receive the flow of pressurized air from a connection port on top of the patient's head and to deliver the flow of pressurized air to the entrance of the patient's airways via the plenum chamber, the at least one gas delivery tube being constructed and arranged to contact, in use, at least a region of the patient's head superior to an otobasion superior of the patient's head, the at least one gas delivery tube comprising a tube wall having an interior passage for flow of pressurized air along a longitudinal axis of the tube to the seal-forming structure, wherein at least a portion of the tube wall comprises:

a patient contacting portion comprising a layer of textile material or foam material configured to lie against the patient's head in use; and a non-patient contacting portion, wherein at least a section of the non-patient contacting portion is comprised of a transparent and/or translucent material to allow viewing of the passage from outside;

wherein the layer of textile material is bonded to the transparent and/or translucent material so that the tube wall is formed as a one piece construction; and wherein a plane extending generally transverse to longitudinal axis contains both (1) the textile material or foam material and (2) the transparent and/or translucent material, so that the patient may view the passage along a transverse axis extending through the plane Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
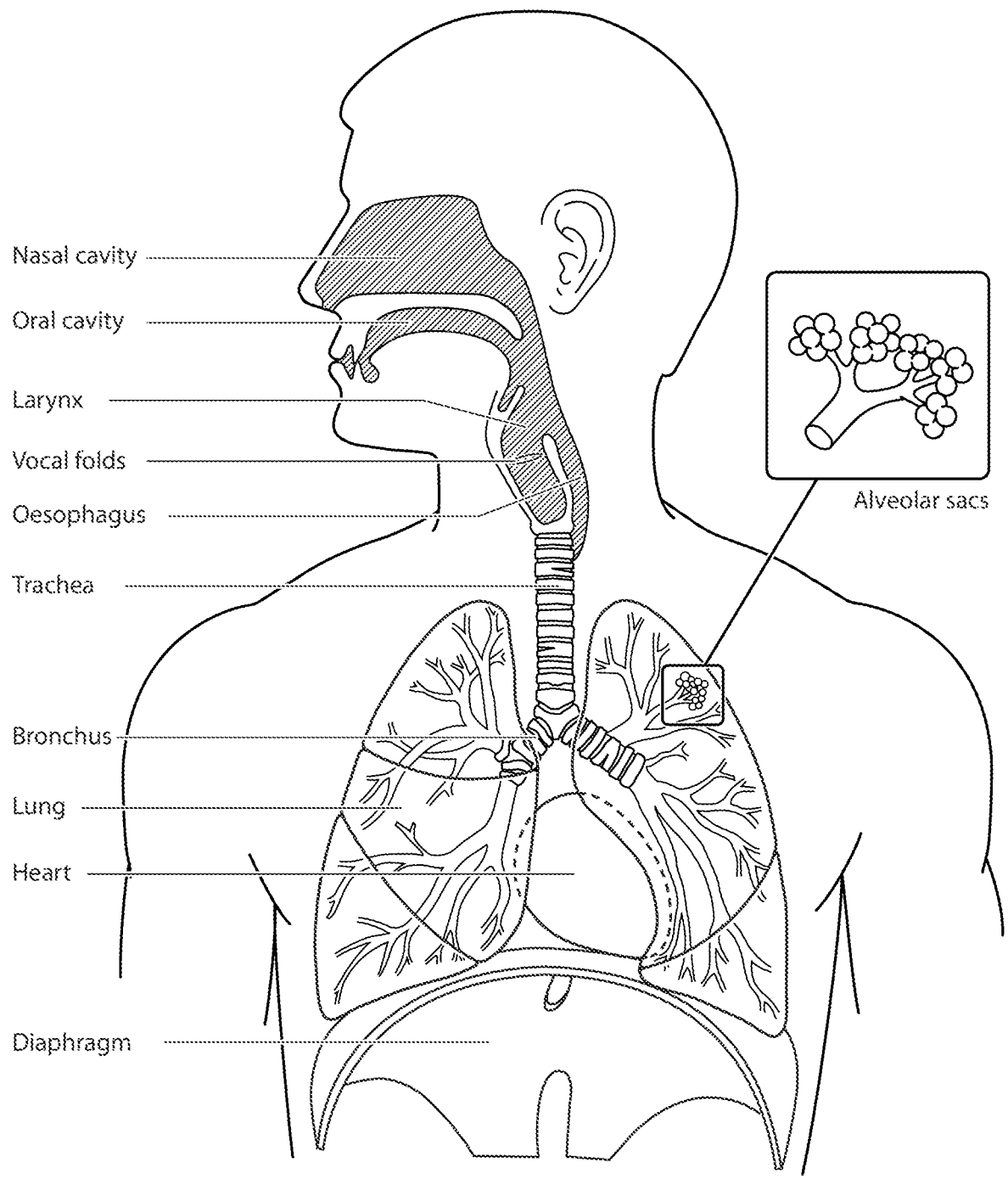
FIG. 2A shows an overview of a human respiratory system including the nasal and oral cavities, the larynx, vocal folds, oesophagus, trachea, bronchus, lung, alveolar sacs, heart and diaphragm.
Figure 2B:
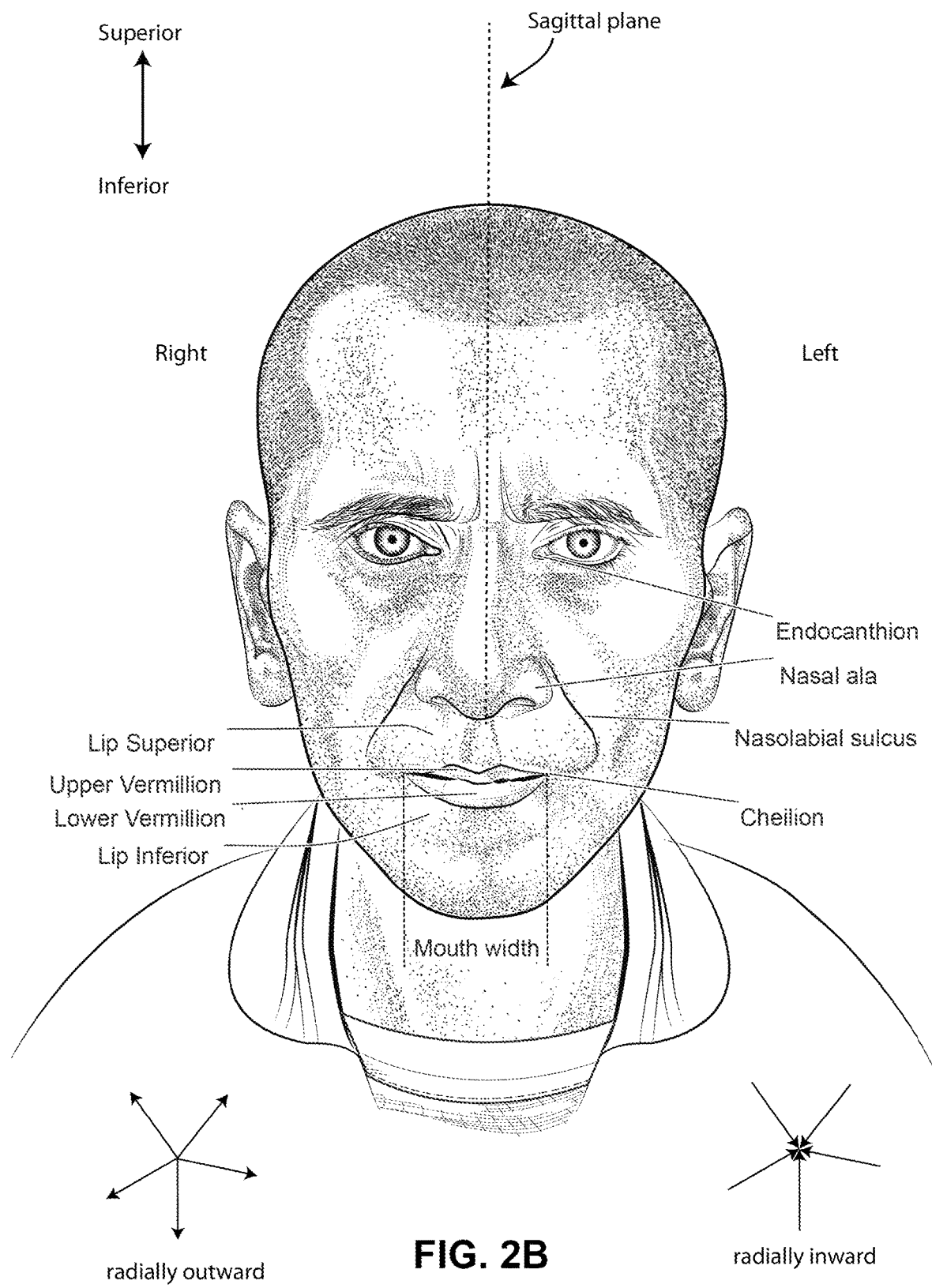
FIG. 2B is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2C:
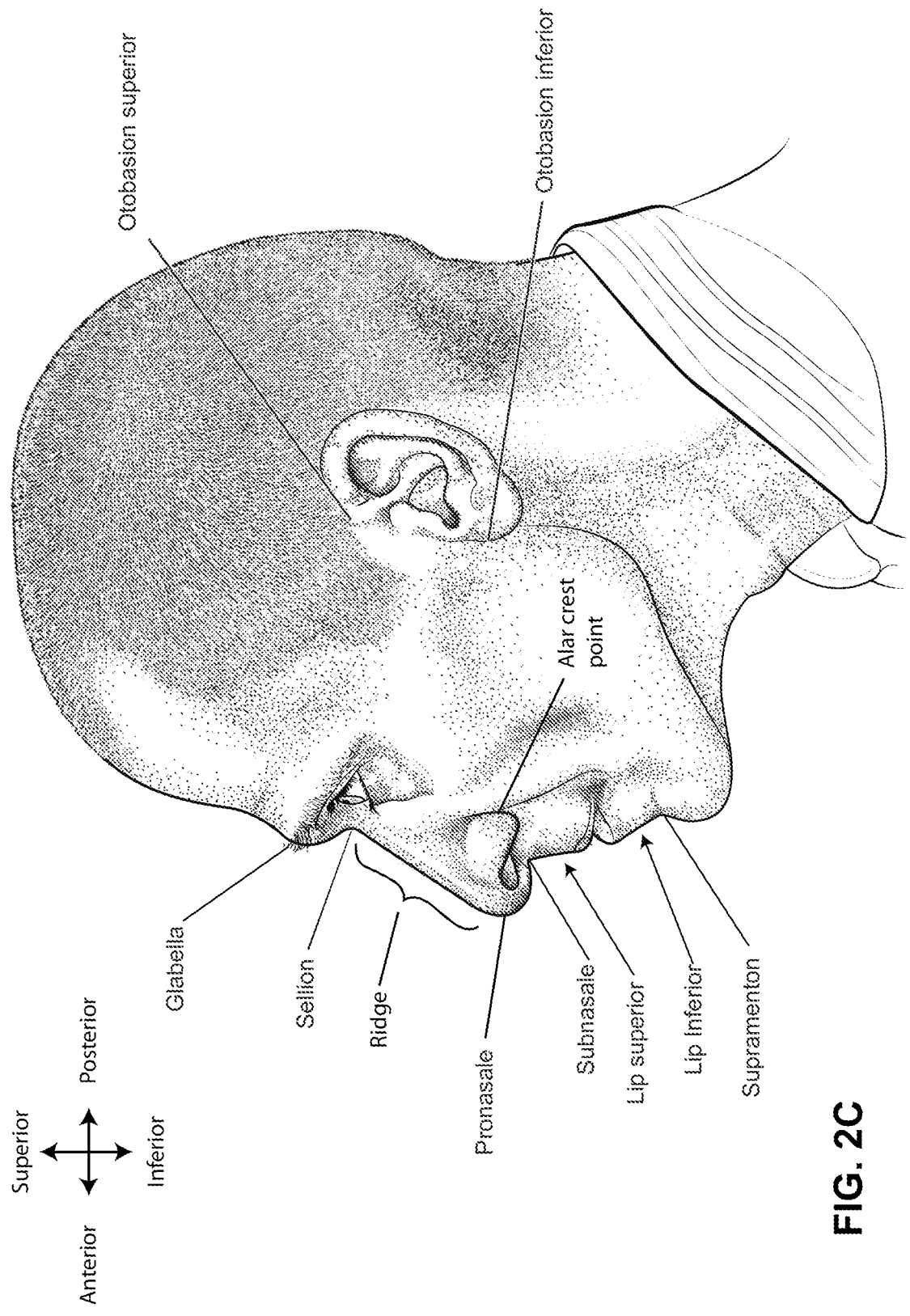
FIG. 2C is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2D:
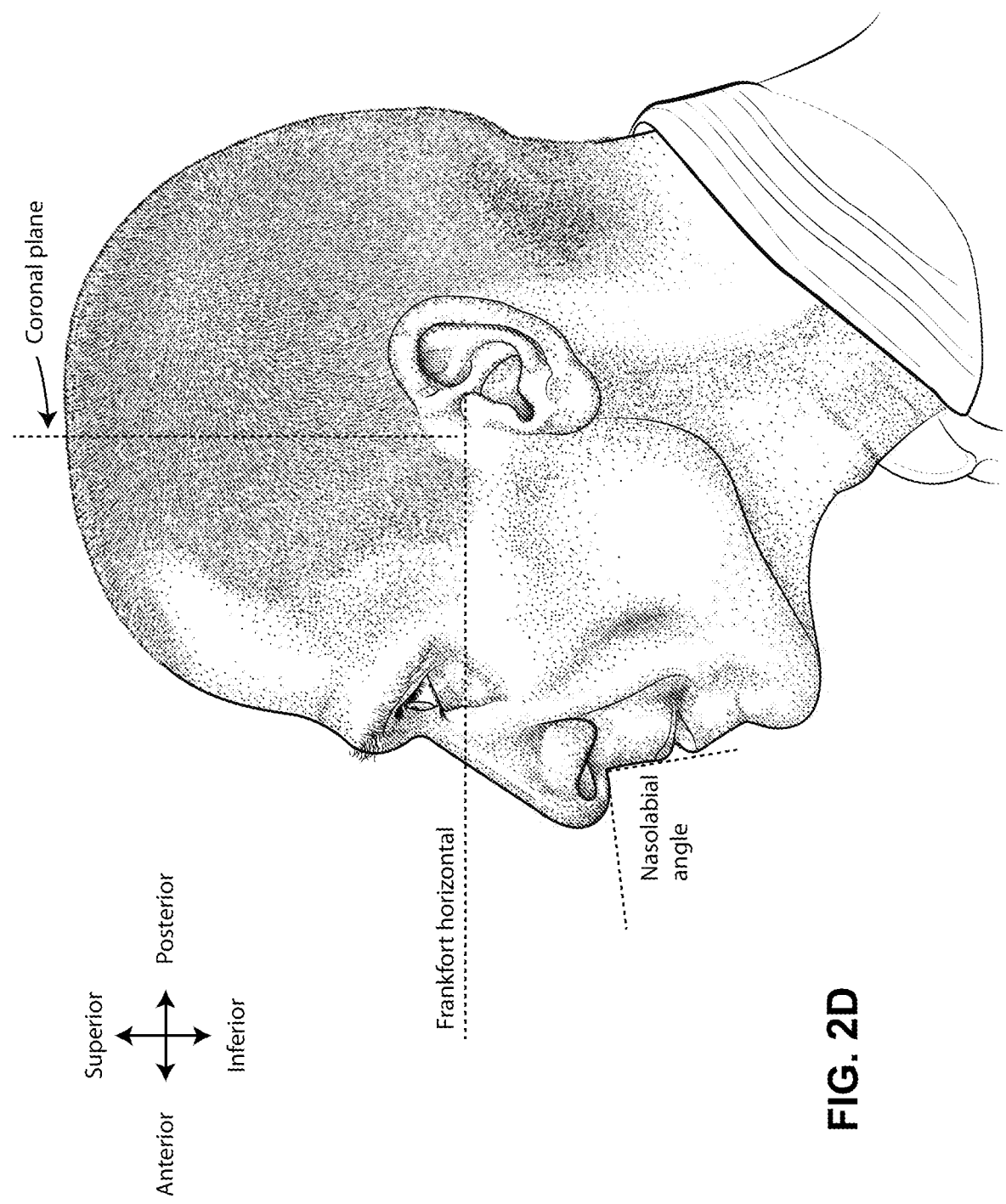

FIG. 2D is a further side view of a head. The approximate locations of the Frankfort horizontal and nasolabial angle are indicated. The coronal plane is also indicated.

3.3 Patient Interface

Figure 3:
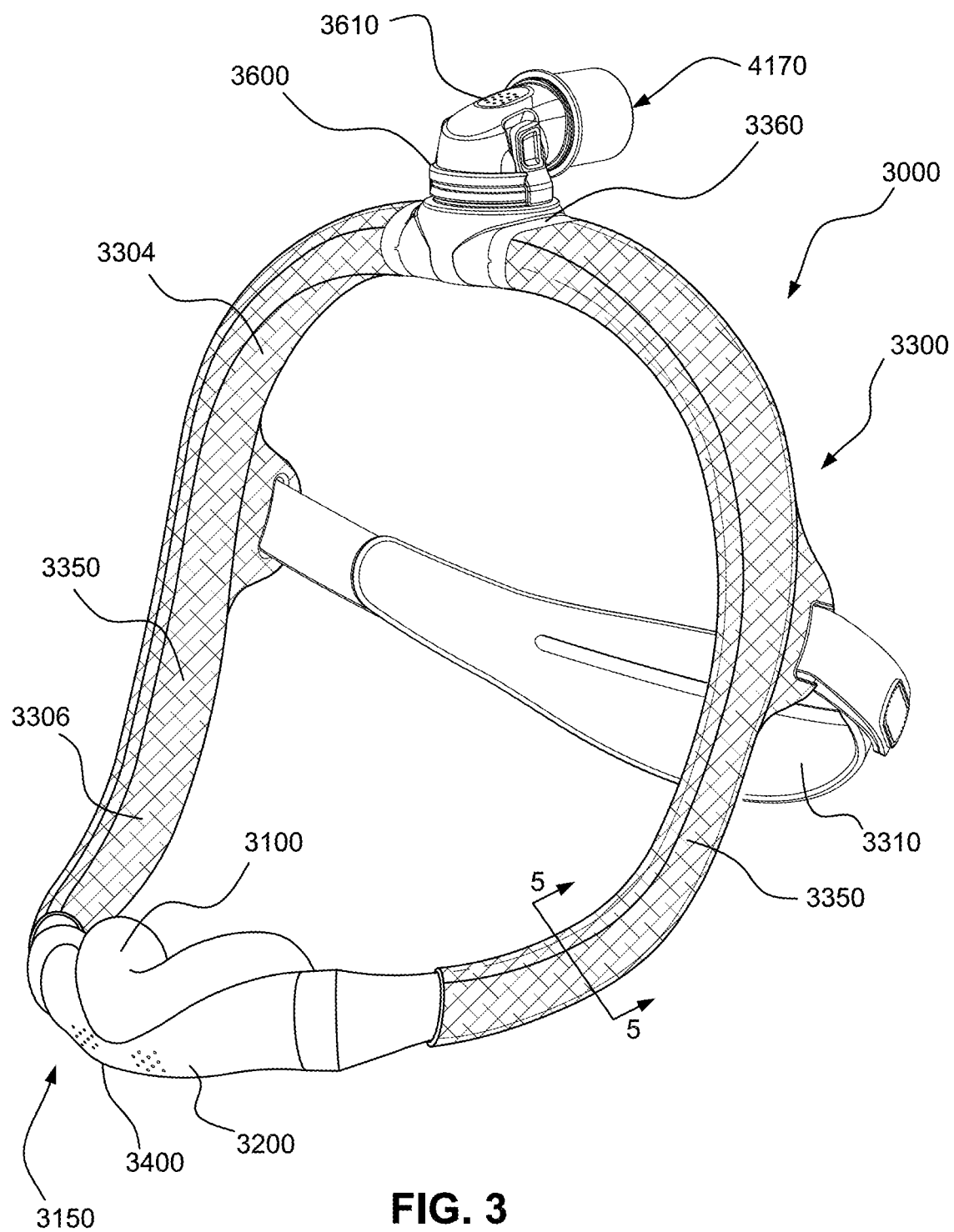

FIG. 3 shows a patient interface in the form of a nasal mask and conduit headgear in accordance with one form of the present technology.

Figure 4:
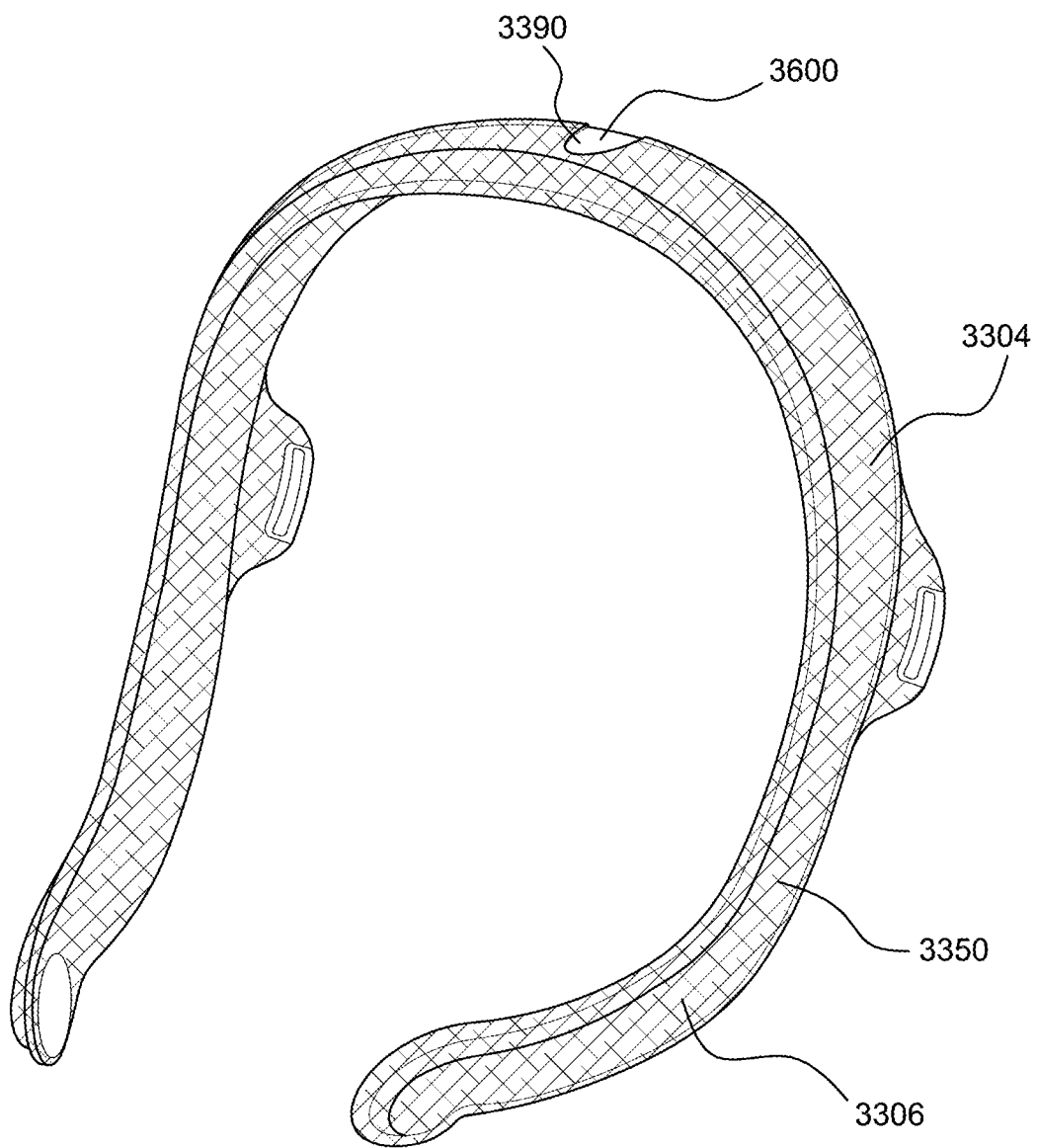

FIG. 4 shows a form of conduit headgear in accordance with another form of the present technology.

Figure 5:
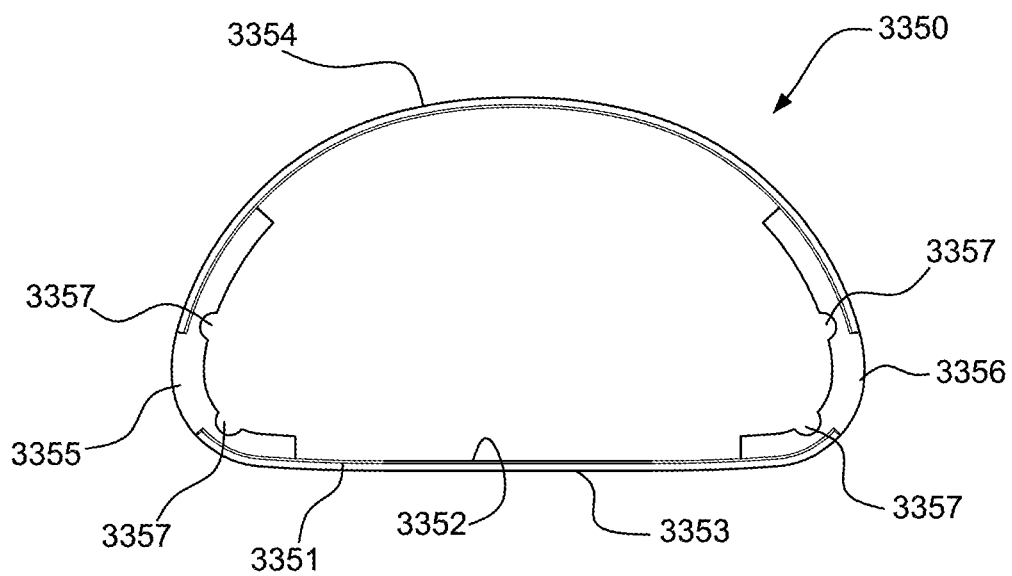

FIG. 5 shows a cross-sectional view of one example of a gas delivery tube in accordance with one form of the present technology.

Figure 6:
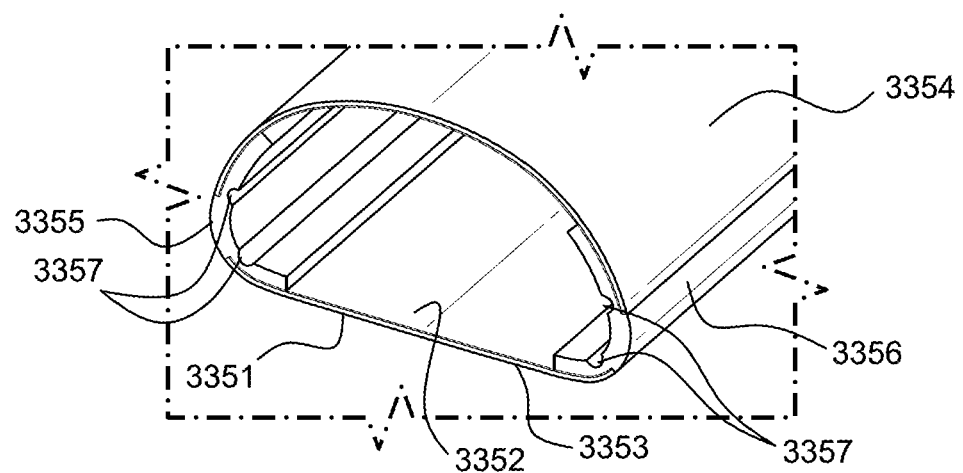

FIG. 6 shows a perspective view of the gas delivery tube of FIG. 5.

Figure 7:
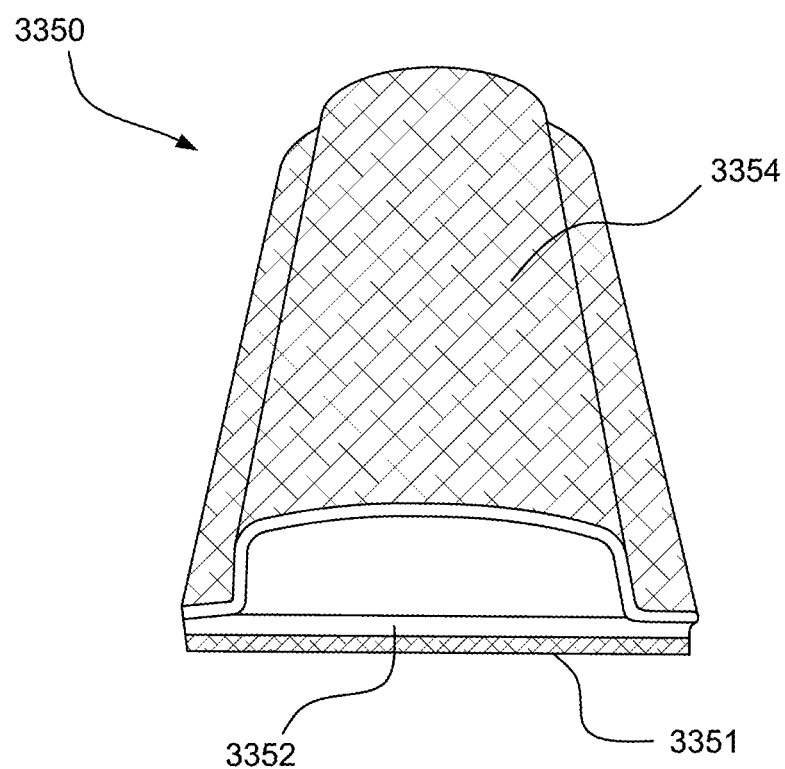

FIG. 7 shows an end view of another example of a gas delivery tube in accordance with another form of the present technology.

Figure 8:
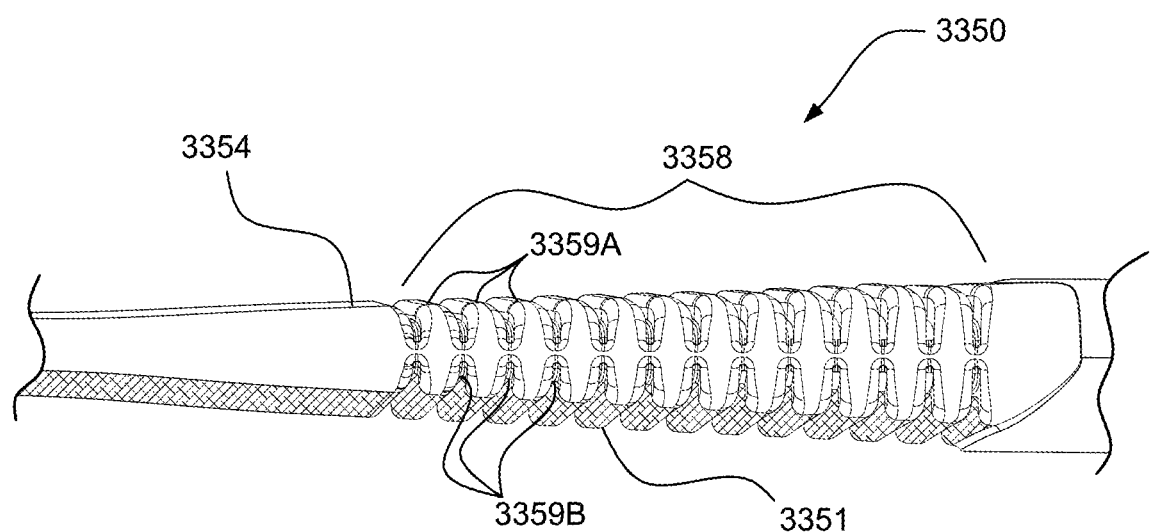

FIG. 8 shows a side view of another example of a gas delivery tube in accordance with another form of the present technology.

Figure 9:
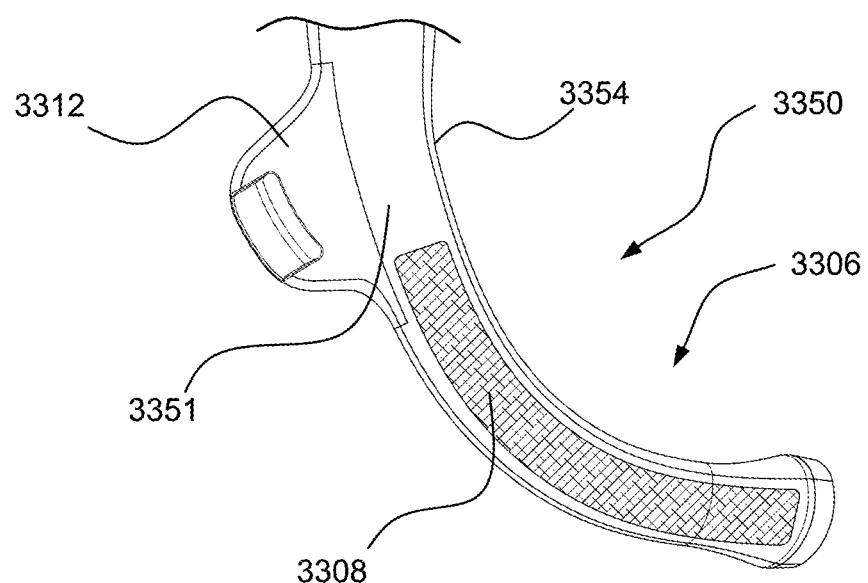

FIG. 9 shows a perspective view of the inferior portion of a gas delivery tube in accordance with another form of the present technology.

Figure 10:
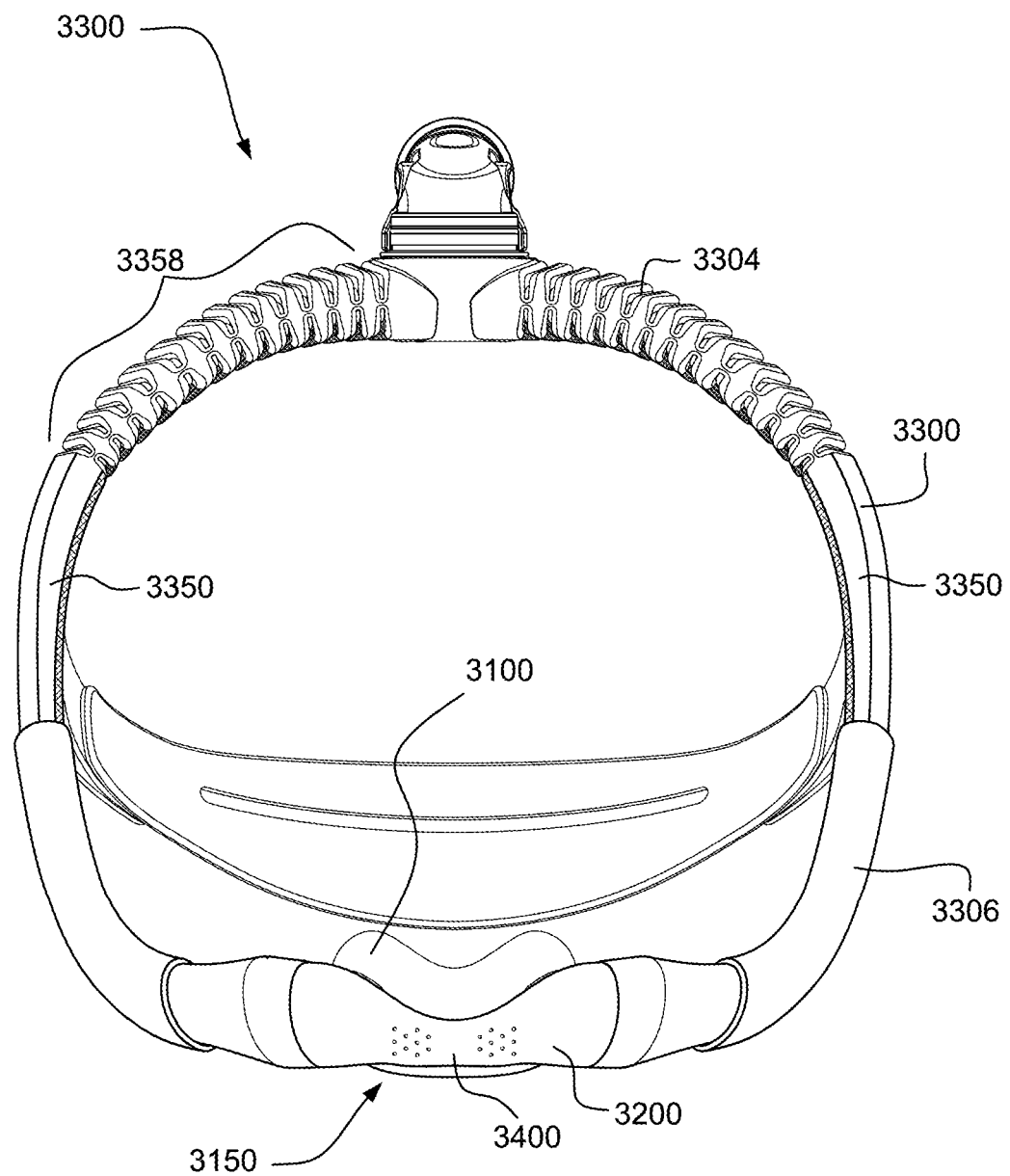

FIG. 10 shows a front view of a form of conduit headgear in accordance with another form of the present technology.

Figure 11:
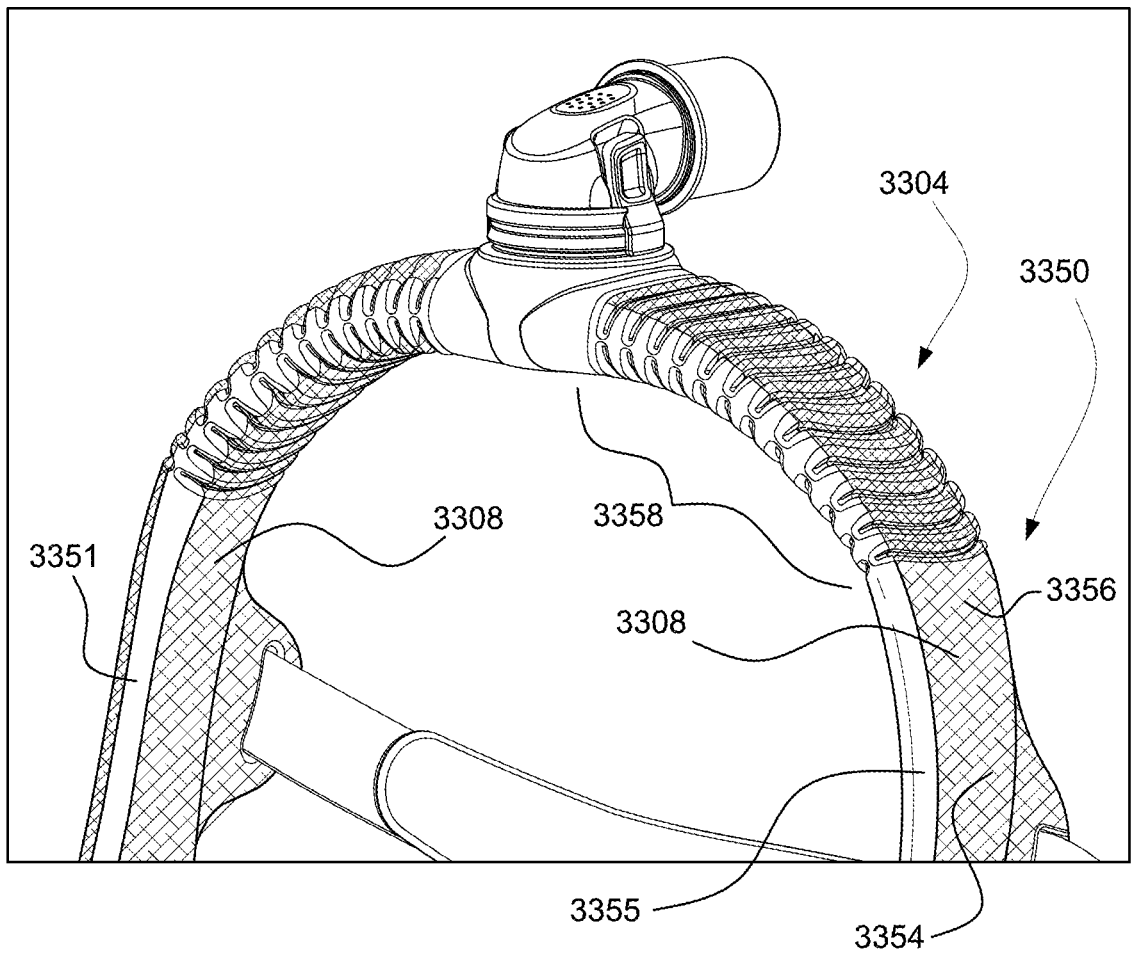

FIG. 11 shows a perspective view of the superior portion of a gas delivery tube in accordance with another form of the present technology.

Figure 12:
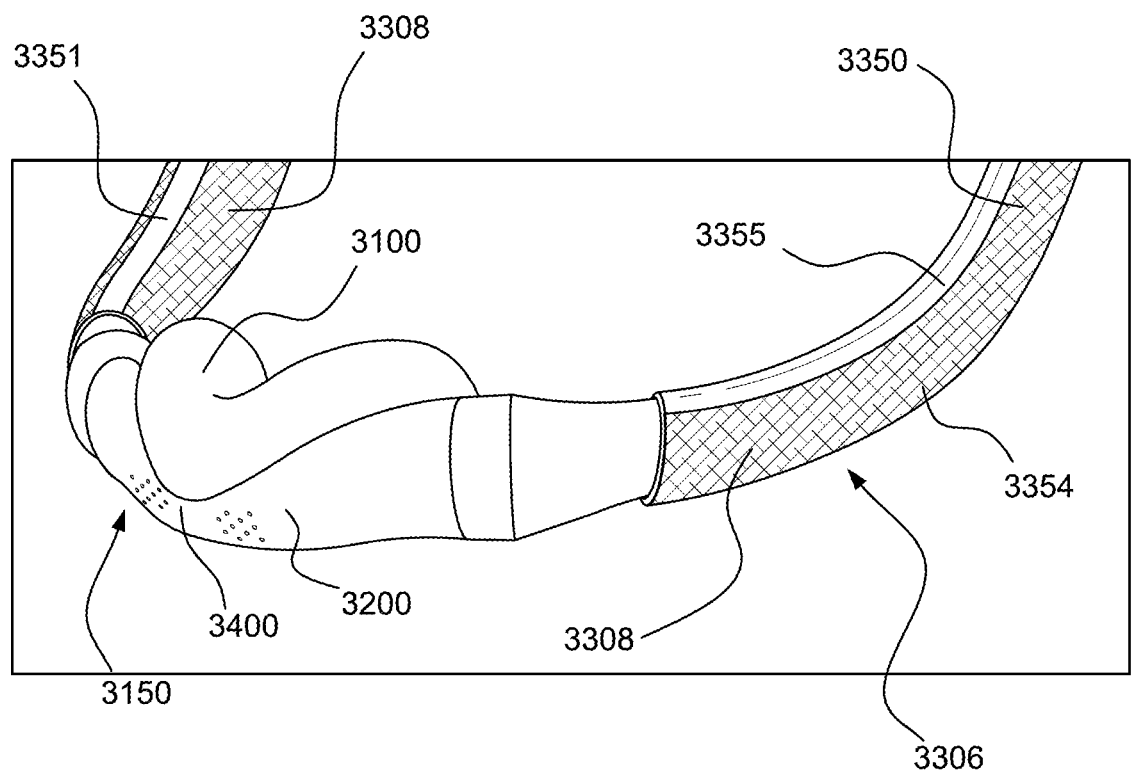

FIG. 12 shows a perspective view of the inferior portion of the gas delivery tube of FIG. 11.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

Figure 1A:
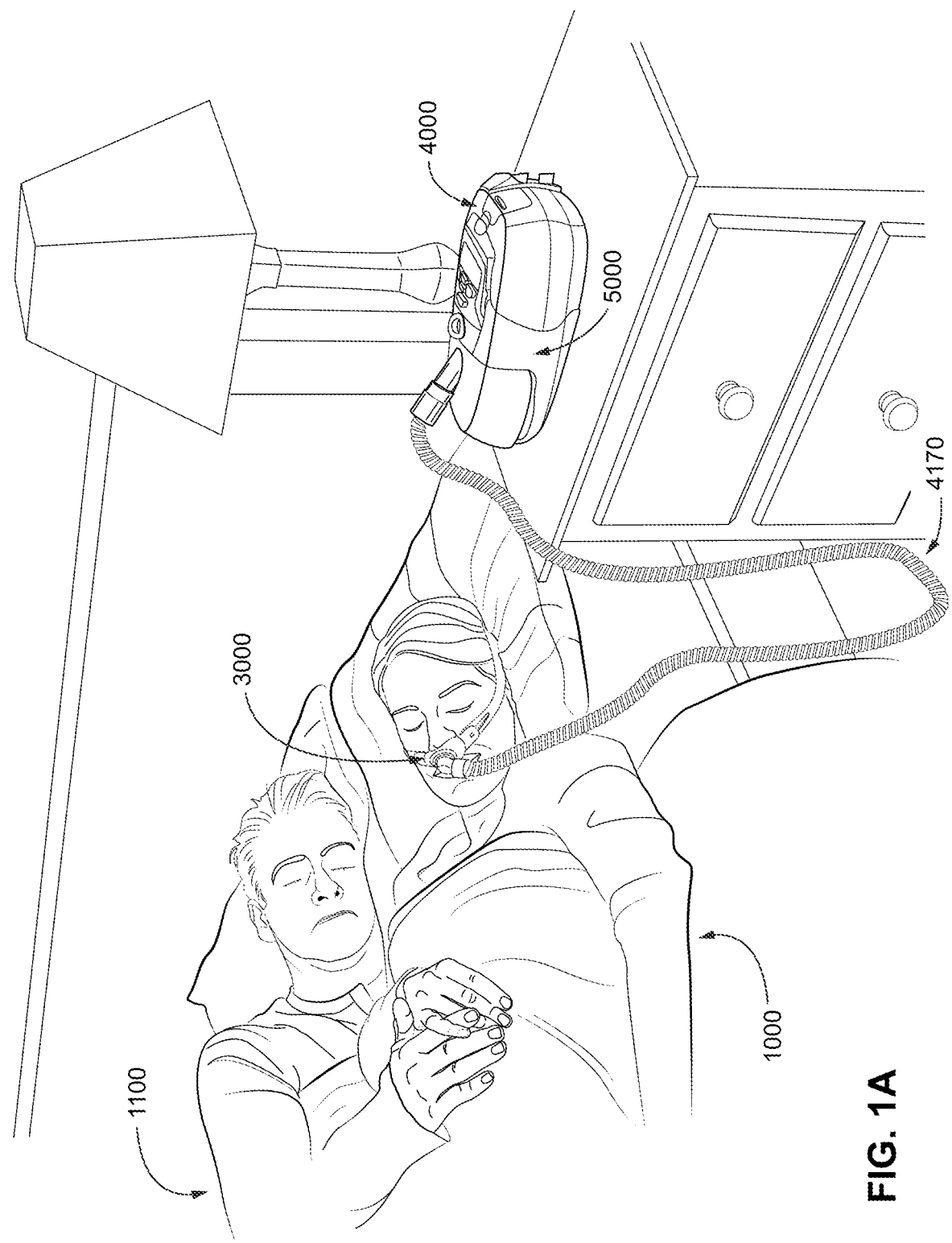
Figure 1B:
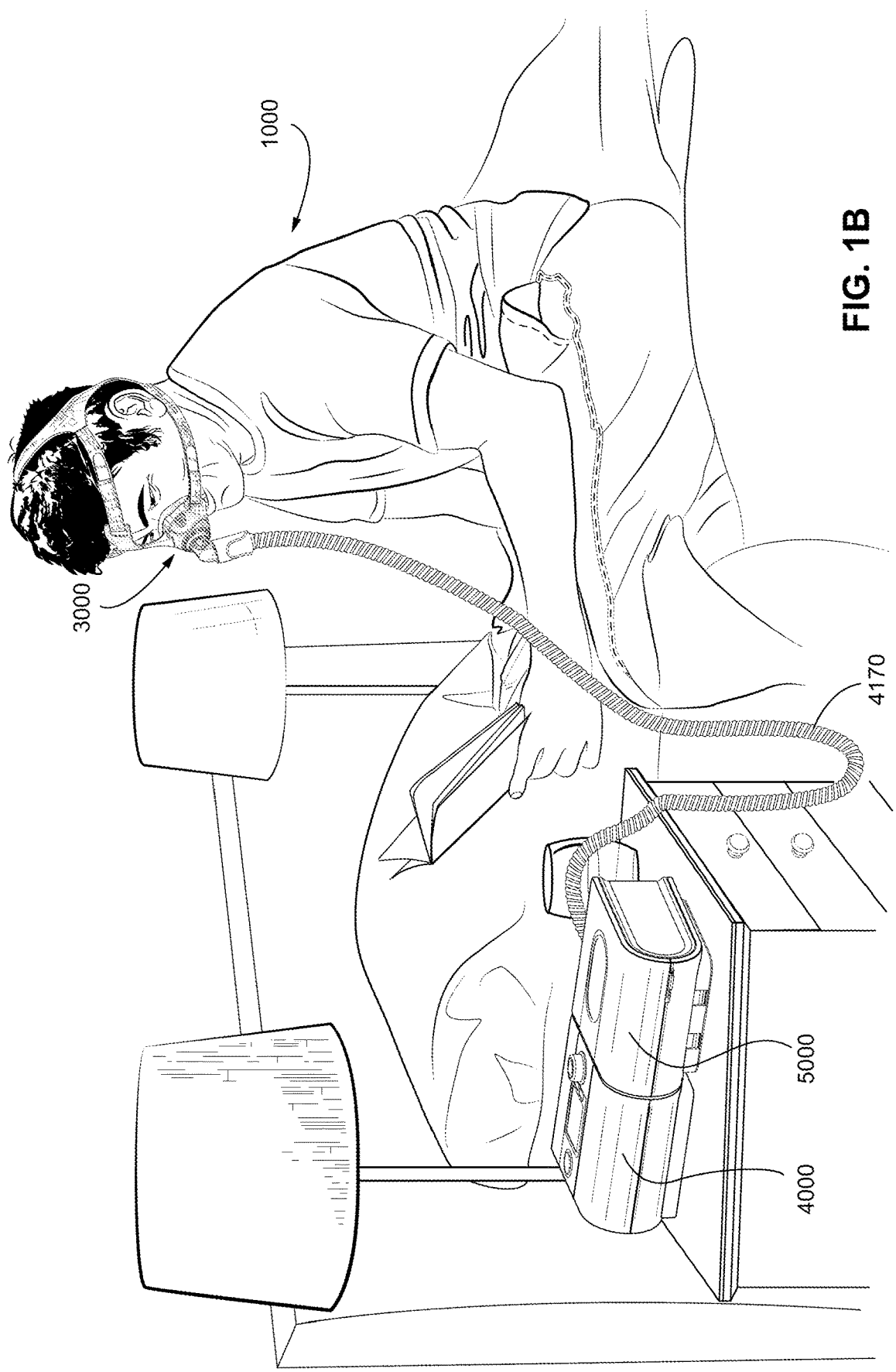
Figure 1C:

With reference to FIG. 3, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit (e.g. the air circuit 4170 shown in FIGS. 1A-1C). In this example, the seal-forming structure 3100 and the plenum chamber 3200 are provided by a cushion module 3150. The cushion module 3150 in this example is a cradle cushion module. In other examples it may be a nasal pillows cushion module or another type of cushion module.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure

3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a pressure activated assisted sealing flange utilizing a pressure assisted sealing mechanism. In use, the pressure assisted sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

In one form, the non-invasive patient interface 3000 comprises a seal-forming structure that forms a seal in use on a nose bridge region or on a nose-ridge region of the patient's face and the upper lip region of the patient's face. In these forms the seal-forming structure may be referred to as a nasal mask. This is the case, for example, with the patient interface 3000 shown in FIG. 1B. This seal-forming portion delivers a supply of air or breathable gas to both nares of patient 1000 through a single orifice. This type of seal-forming structure may be referred to as a "nasal cushion" or "nasal mask". In some examples of the present technology, the positioning and stabilising structure 3300 shown in FIG. 3 or 4 may be utilised to hold a nasal cushion in sealing position on a patient's face.

In one form, for example as shown in FIG. 3, the seal-forming structure 3100 is configured to form a seal in use with the underside of the nose around the nares and optionally with the lip superior of the patient 1000. This type of seal-forming structure may be referred to as a "cradle cushion" or "sub-nasal mask". The shape of the seal-forming structure may be configured to match or closely follow the underside of the patient's nose, i.e. the profile and angle of the seal-forming structure may be substantially parallel to the patient's naso-labial angle. In one form of nasal cradle cushion, the seal-forming structure comprises a bridge portion defining two orifices, each of which, in use, supplies air or breathable gas to a different one of the patient's nares. The bridge portion may be configured to contact or seal against the patient's columella in use. In some forms of the technology, the seal-forming structure 3100 is configured to form a seal on an underside of the patient's nose without contacting a nasal bridge region of the patient's nose. In some examples, patient interface may comprise a seal-forming structure 3100 in the form of a cradle cushion as described in PCT Application No. PCT/AU2018/050289, filed Mar. 29, 2018, the entire contents of which are incorporated herein by reference.

In one form the patient interface 3000 comprises a seal-forming portion that forms a seal in use on a chin-region, a nasal bridge region and a cheek region of the patient's face. This is the case, for example, with the patient interface 3000 shown in FIG. 1C. This seal-forming portion delivers a supply of air or breathable gas to both nares and mouth of patient 1000 through a single orifice. This type of seal-forming structure may be referred to as a "full-face mask". In some examples of the present technology, the positioning and stabilising structure 3300 shown in FIG. 3 or 4 may be utilised to hold a full-face cushion in sealing position on a patient's face. Alternatively, the positioning and stabilising structure 3300 of FIG. 3 or 4 may be used with a patient interface 3000 that comprises a nasal seal-forming structure in the manner of a nasal cushion or nasal cradle cushion and an oral seal-forming structure that is configured to form a seal in use around the mouth of a patient (which may be referred to as a "mouth cushion" or "oral mask"). In such a mask air or breathable gas is supplied in use through orifices to the patient's nares and the patient's mouth. This type of seal-forming structure 3100 may be referred to as an "oro-nasal cushion", where there are separate sealing portions around the mouth and nose, or "ultra-compact full face cushion", where the sealing of the nose is around or close to the patient's nares. In one form, the nasal seal-forming structure and oral seal-forming structure are integrally formed as a single component. In some examples, patient interface may comprise a seal-forming structure 3100 in the form of a cradle cushion as described in U.S. Patent Application No. 62/649,376, the entire contents of which are incorporated herein by reference.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, such as in the patient interface 3000 of FIG. 3, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300. Positioning and stabilising structure 3300 may be referred to as "headgear" since it engages the patient's head in order to hold the patient interface 3000 in a sealing position.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

A tie will be understood to be a structure designed to resist tension. In use, a tie may be part of the positioning and stabilising structure 3300 that is under tension. Some ties will impart an elastic force as a result of this tension, as will be described. A tie may act to maintain the seal-forming structure 3100 in a therapeutically effective position on the patient's head.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone. The first tie may be provided, for example, as part of a patient interface that comprises a cradle cushion, nasal pillows, nasal cushion, full-face cushion or an oronasal cushion. For example, the positioning and stabilising structure 3300 of FIG. 3 comprises a first tie in the form of gas delivery tubes 3350 which lie over the top of the patient's head. The gas delivery tubes 3350 may also be known as headgear tubes 3350 as they provide functions of headgear.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head. The second tie may be provided, for example, as part of a patient interface that comprises a cradle cushion, nasal pillows, full-face cushion, nasal cushion or an oronasal cushion. For example, the positioning and stabilising structure 3300 of FIG. 3 comprises a second tie in the form of a strap 3310 that lies against posterior surfaces of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another. Additionally, in some forms the positioning and stabilising structure comprises a fourth tie that is constructed and arranged to interconnect the second tie and the third tie to reduce a tendency of the second tie and the third tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping. The positioning and stabilising structure 3300 of FIG. 3 comprises a strap 3310 that is bendable. The strap 3310 may be considered a backstrap. The strap 3310 is sufficiently flexible to pass around the back of the patient's head and lie comfortably against the patient's head, even when under tension in use.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another suitable for a small sized head, but not a large sized head.

5.3.3.1 Headgear Tubing

In some forms of the present technology, the positioning and stabilising structure 3300 comprises one or more tubes 3350 that deliver pressurised air received from a conduit forming part of the air circuit 4170 from the RPT device to the patient's airways, for example through the plenum chamber 3200 and seal-forming structure 3100. In the form of the present technology illustrated in FIG. 3, the positioning and stabilising structure 3300 comprises two separate gas delivery tubes 3350 that deliver air to the seal-forming structure 3100 from the air circuit 4170. The tubes 3350 are an integral part of the positioning and stabilising structure 3300 of patient interface 3000 to position and stabilise the seal-forming structure 3100 of the patient interface to the appropriate part of the patient's face (for example, the nose and/or mouth). This allows the conduit of air circuit 4170 providing the flow of pressurised air to connect to a connection port 3600 of the patient interface in a position other than in front of the patient's face which may be unsightly to some people. While a pair of tubes 3350 have some advantages (described below), in some examples, the positioning and stabilising structure 3300 comprises only a single tube 3350 configured to overlie the patient's head on one side. A strap or other stabilising component may be provided to the other side of the patient's head between the top end of the single tube 3350 and the seal-forming structure 3100, to provide balanced forces on the seal-forming structure 3100.

Since air can be contained and passed through headgear tubing 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIG. 3, the positioning and stabilising structure 3300 comprises the headgear tubing 3350, which is inflatable, and the strap 3310, which is not inflatable.

In certain forms of the present technology, the patient interface 3000 may comprise a connection port 3600 located proximal a top, side or rear portion of a patient's head. For example, in the form of the present technology illustrated in FIG. 3, the connection port 3600 is located on top of the patient's head. In this example the patient interface 3000 comprises an elbow 3610 to which the connection port 3600 is provided. The elbow 3610 may swivel with respect to the positioning and stabilising structure 3300 and order to decouple movement of a conduit connected to the connection port 3600 from the positioning and stabilising structure 3300. The connection port may be configured as a fluid connection opening 3390, as shown in FIG. 4, in the headgear tubing 3350 or to a component to which the headgear tubing 3350 is connected as in FIG. 3. Additionally, or alternatively, a conduit connected to the connection port 3600 may swivel with respect to the elbow 3610. In the illustrated example, elbow 3610 comprises a swivelling conduit connector comprising the connection port 3600 to which a conduit of the air circuit 4170 is able to connect, such that the conduit can rotate about its longitudinal axis with respect to the elbow 3610. In the example of FIG. 4, the air circuit 4170 may connect to the fluid connection opening. The elbow 3610 may rotatably connect to the fluid connection opening or to a ring received in the fluid connection opening.

Patient interfaces in which the connection port 3600 is not positioned in front of the patient's face may be advantageous as some patients find a conduit that connects to a patient interface 3000 in front of the face to be unsightly and/or obtrusive. For example, a conduit connecting to a patient interface 3000 in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the forms of the present technology illustrated in FIGS. 3 and 4, the positioning and stabilising structure 3300 comprises two tubes 3350, each tube 3350 being positioned in use on a different side of the patient's head and extending across the respective cheek region, above the respective ear (superior to the otobasion superior on the patient's head as indicated in FIG. 2C) to the elbow 3610 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

The positioning and stabilising structure may alternatively be provided as a single gas delivery tube having left and right arms, as shown in FIG. 4. In the illustrated example, the connection port 3600 is provided to the superior side of the positioning and stabilising structure rather than being a separate connection module as in the example of FIG. 3.

In a certain form of the present technology, the patient interface 3000 is configured such that the connection port 3600 is positioned approximately at a top point of the patient's head. The connection port 3600 may be positioned in the sagittal plane and aligned with the otobasion superior points in a plane parallel to the coronal plane. The otobasion superior points are identified in FIG. 2C. In some forms of the technology, the positioning and stabilising structure 3300 is configured to be worn in different positions, with the effect that the connection port 3600 may be positioned proximate the top of the patient's head in the sagittal plane up to around 20 mm forward or 20 mm rearward of the otobasion superior points.

As described above, in some examples of the present technology the patient interface 3000 comprises a seal-forming structure 3100 in the form of a cradle cushion which lies generally under the nose and seals to an inferior periphery of the nose. The positioning and stabilising structure 3300 may be structured and arranged to pull the seal-forming structure 3100 into the patient's face under the nose with a sealing force vector that has a posterior and superior direction (e.g. a posterosuperior direction). A sealing force vector with a posterosuperior direction may facilitate the seal-forming structure 3100 forming a good seal to both the inferior periphery of the patient's nose and the anterior-facing surfaces of the patient's face on either side of the patient's nose and the upper lip.

In some examples, the positioning and stabilising structure 3300 may in use apply a sealing force vector having a posterosuperior direction at an angle of approximately 35° with respect to the patient's Frankfort horizontal (identified in FIG. 2D). The superior portions of the tubes 3350 (e.g. the portions of the tubes 3350 superior to the strap 3310) may be oriented vertically, and the rear headgear strap 3310 may extend from the tubes 3350 in a posteroinferior direction at an angle of approximately 35° with respect to the patient's Frankfort horizontal. In this particular setup, there is an angle θ of 125° formed between the strap 3310 and the superior portions of the tubes 3350 where the strap 3310 connects to the tubes 3350. In other examples, θ may be greater or less than 125°.

In the forms of the technology shown in FIGS. 3 and 4 the two tubes 3350 are fluidly connected at their upper ends to each other and to the connection port 3600. In FIG. 3, the tubes 3350 are separate tubes that are connected to a crown connector 3360. The tubes 3350 are indirectly connected to each other by the crown connector 3360 and may be disconnected, for example for cleaning, storage or replacement. In FIG. 4, the two tubes are integrally formed and the connection port 3600 is comprised as a fluid connection opening 3390 to which a swivel elbow connects. In other examples where separate tubes are used they may be indirectly connected together, for example each may be connected to a T-shaped conduit having two conduit arms each fluidly connectable to the tubes 3350. The crown connector 3360 may comprise a third conduit arm. The connection port 3600 may comprise an elbow 3610 received in the fluid connection opening 3390 at the centre of the crown connector 3360. The elbow 3610 may be received in a ring in the fluid connection opening 3390 and may be configured to swivel within the ring. The fluid connection opening 3390 may be also considered a connection port 3600 itself.

The tubes 3350 in the form of the technology shown in FIGS. 3 and 4 have a length of between 15 and 30 cm each, for example between 20 and 27 cm each. The length of the tubes is selected to be appropriate for the dimensions of the heads of typical patients, for example the distance between the region proximate the top of the head where the upper end of the tubes 3350 are situated, and the region proximate the openings to the patient's airways at which the lower end of the tubes 3350 connect to the plenum chamber 3200 when following a generally arcuate path down the sides of the heads and across the patient's cheek region (such as the arcuate path taken by the tubes 3350 shown in FIGS. 3 and 4). In some examples, the patient interface 3000 may be configured so that the length of the tubes 3350 can be varied. It will be appreciated that the length of the tubes 3350 will depend on the length of other components in the patient interface 3000, for example the length of the crown connector 3360 to which the superior ends of the tubes 3350 connect and/or the size of the plenum chamber 3200.

The cross-sectional shape of the gas delivery tubes 3350 may be circular, elliptical, oval, D-shaped, trapezoidal or a rounded rectangle, for example as described in U.S. Pat. No. 6,044,844, the contents of which are incorporated herein by way of reference. A cross-sectional shape that presents a flattened surface of tube on the side that faces and contacts the patient's face or other part of the head may be more comfortable to wear than, for example a tube with a circular cross-section.

The cross-sectional width and/or height of the tubes 3350 may be in the range 8-35 mm. In some forms in which the tubes have an approximately D-shaped cross-section, the tubes may have a width in the range 15-25 mm, and a height in the range 6-15 mm. The height may be considered to be the dimension of the tube extending away from the patient's face in use, i.e. the distance between a patient contacting portion 3348 and the outermost part of a non-patient contacting portion 3349, while the width may be considered to be the dimension across the surface of the patient's head. The cross-sectional thickness of the material forming the tubes 3350 may be in the range 0.8-1.6 mm, for example 1.0-1.5 mm.

5.3.3.1.1 Gas Delivery Tube Construction

In an example of the present technology, FIG. 5 shows a cross-section through a gas delivery tube 3350 having a substantially D-shaped profile. In use, the flat side of the profile contacts the patient's face and head and should be understood to be the patient contacting portion of the gas delivery tube. The raised or arcuate side of the profile should be understood to be the non-patient contacting portion of the gas delivery tube. In some examples, the gas delivery tube may have a more square or rectangular shaped profile, configured with slightly rounded corners for patient comfort.

The gas delivery tube 3350 is constructed at least substantially of a textile material and/or a foam material, and a transparent material, comprised at least substantially of an elastomeric material. The transparency of the elastomeric material, i.e. its transmittancy of light, is such it can be seen through. In some examples, the transparency may be high, with minimal or no deflection of transmitted light, such that the transparency of the elastomeric material is analogous to glass or film. In other examples, the transparency may have some limited deflection of transmitted light, such that the transparency of the elastomeric material is somewhat hazy but sufficient for the patient to detect obvious dirt and mould.

In use, the gas delivery tube is constructed such that the patient contacting portion of the gas delivery tube, i.e. the portion that contacts the patient's face and head, is comprised substantially of the textile material. The transparent material comprises at least part of the non-patient contacting side of the gas delivery tube.

This construction provides a gas delivery tube that is comfortable for the patient to wear as part as of a positioning and stabilising structure while also allowing for the inspection of the interior of the gas delivery tube. This may mean build-up of dirt or mould or the like within the interior of the gas delivery tube can be visibly detected. The patient may disconnect the gas delivery tube 3350 from the plenum chamber 3200 in order to remove any debris detected within the interior. When the gas delivery tube is being cleaned, the transparent material allows the patient to confirm that any dirt and mould has been removed.

In certain forms of the present technology, the gas delivery tube 3350 is constructed from a translucent material. The use of a translucent material may function in substantially the same way as the transparent material, and may be used in addition to, or instead of, the transparent material in any embodiment.

A further advantage of this construction is the textile material and elastomeric material may combine for an integrated look and feel, providing a potentially higher perception of quality compared to conventional gas delivery tubes constructed entirely of textile materials or elastomeric materials. Additionally, the integrated construction may provide a low cost and light weight product compared to conventional gas delivery tubes.

5.3.3.1.2 Textile/Foam Material

The flat side 3351 of the gas delivery tube 3350 forms the patient contacting side 3351 of the gas delivery tube. It is comprised of a textile material. In this example, the textile material may have at least two layers; an inner layer 3352 comprised of a gas impermeable layer, for example formed from a film or laminate of silicone or another elastomeric plastics material, such as TPE or TPE; and an outer textile layer 3353 forming the exterior of the gas delivery tube 3350. The inner layer 3352 is bonded to the outer textile layer 3353. In some other examples, there may be additional layers provided between the gas impermeable later and the outer textile layer, for example, an intermediary adhesive layer bonding the gas impermeable layer to the outer textile layer 3353. In yet further examples, the textile material may comprise a single layer. In these examples, the textile material may be inherently gas impermeable such that an additional film or laminate layer is not required.

In some examples of the present technology, such as the examples shown in FIGS. 3 and 4, the headgear tubes 3350 comprise a patient-contacting side that is formed at least partially from a textile material as described previously. Additionally or alternatively, the patient-contacting side of the gas delivery tubes 3350 may be formed from a foam material. In some examples the tubes 3350 comprise a combination of textile and foam materials. The textile and/or foam materials comprising the patient-contacting side of the gas delivery tubes may: hold air under pressure, be biocompatible and suitable/approved for use in forming a medical air path, be lighter than silicone tubes, be soft and flexible, generally retain a predetermined shape, be cleanable and be durable for a predetermined lifecycle such as one month, three months, six months, a year or longer.

As previously discussed, the arcuate side 3354 of the D-shaped profile forms the non-patient contacting portion 3354 of the gas delivery tube. In one example, at least a section of the non-patient contacting portion is comprised in the same way as the patient contacting side, i.e. a textile material having at least two layers; an inner layer comprised of a gas impermeable layer formed from an elastomeric plastics material bonded to an outer textile layer. However, in other examples, the textile material that may comprise part of the non-patient contacting portion may be sufficiently gas impermeable such that no inner layer is required and the non-patient contacting portion comprises a single layer of textile material and the transparent material. The textile material of the non-patient contacting side 3354 may be stiffened (e.g., by the gas impermeable layer, by an added stiffener, etc.) in order to assist in maintaining the acuate shape. Alternatively, no stiffeners may be included, and the arcuate D-shape may only be formed when pressurized air flows through the gas delivery tube 3350.

In one example, the textile material that comprises the gas delivery tube may be a blend of polyamide, for example, a nylon, polyester and/or spandex, and weighted from between 50 g/m² to 250 g/m². In a further example, the textile material may be of a material weighted to 120 g/m². In some examples, the inner layer of the textile material may comprise two or more laminate coats of silicone. In one example, each laminate coat of silicone may be between 5 to 75 microns thick. In a further example, each laminate coat of silicone may be between 20 to 30 microns thick, preferably 25 microns thick.

Having a textile exterior to both the patient contacting and non-patient contacting sides of the gas delivery tube is advantageous. On the patient contacting side, it is more comfortable when contacting the face while on the non-patient contacting side, there is less friction when the gas delivery tube contacts other textiles, such as pillows or bed linen when wearing the patient interface in bed. It is also more aesthetically pleasing to the touch.

5.3.3.1.3 Transparent Material—Window Sections

In the example of FIGS. 5 and 6, the anterior and posterior sides of the D-shaped profile, where the patient contacting side of the gas delivery tube 3350 and the non-patient contacting side of the gas delivery tube 3350 meet, are formed from a transparent material. This transparent material forms window sections in the profile of the gas delivery tube 3350 which enables the user to visibly inspect its interior. This allows for easier detection of build-up of mould and/or dirt and facilitates better cleaning of the interior while still retaining the comfort of a substantially textile exterior.

In the example of FIGS. 5 and 6, both the patient contacting side 3351 and non-patient contacting side 3354 of the gas delivery tube 3350 are each formed from a single strip of textile material. Furthermore, the gas delivery tube of FIGS. 5 and 6 is configured with two window sections, one window section along each of the anterior and posterior sides of the gas delivery tube. In the illustrated example, a transverse axis TA may extend through both the anterior side and the posterior side in a direction transverse to a longitudinal axis LA, which extends generally along at least a portion of the gas delivery tube 3350 (e.g., along the interface between the plenum chamber 3200 and the positioning and stabilising structure 3300) in a direction of the flow of pressurized air. The transverse axis may not pass through either strip of textile material. For example, the transverse axis may extend along the strip of textile material that forms the patient contacting side 3351 in the anterior/posterior direction, but does not intersect the strip of textile material that forms the non-patient contacting side 3354. A patient looking along the transverse axis TA may be able to see entirely through the gas delivery tube 3350. In other words, the gas delivery tube 3350 includes no opaque material when viewed along the transverse axis TA. The patient may be able to more clearly identify and debris within the gas delivery tube 3350, because said debris may block a clear line of sight along the transverse axis TA.

However, the both textile and transparent material are included along a perimeter of the gas delivery tube 3350, so that a transverse plane (i.e., a plane including the transverse axis TA) to the longitudinal axis LA (i.e., cross-section viewed in FIG. 5) includes both the transparent material and the textile material in an orientation that is exposed to a patient (e.g., for visual inspection).

Each strip of textile material has opposing edges along its elongate dimension; the transparent material of the window sections are bonded to the respective edges of the patient contacting side 3351 and non-patient contacting side 3354, using adhesives or heat welding techniques. In other examples, the window sections may be overmoulded to the edges of the textile material of the patient contacting side 3351 and non-patient contacting side 3354.

In other examples, the non-patient contacting side 3354 may be formed from two or more strips of textile material interspersed with a transparent material. For example, the non-patient contacting side 3354 may be formed from two strips of textile material, separated by a single strip of transparent material, bonded or overmoulded to the respective edges of the textile material. In addition to the window sections 3355, 3356 at either side of the D-shaped profile, this places a window section in the centre of the arcuate side of the D-shaped profile. In yet another example, the patient contacting and non-patient contacting side of the gas delivery tube is formed from a single strip of textile material, the edges of the textile material being positioned substantially centrally on the non-patient contacting side 3354 of the D-shaped profile or alternatively to one side. The window section in this example is positioned between the elongate edges of the textile material. In other words, the transparent material is positioned (e.g., overmolded) between the elongated edges of the textile material, so that the edges do not completely connect. In this example, a patient would have only a single viewing window, and would be unable to see completely through the gas delivery tube 3350.

In these examples, the transparent material forming the window sections 3355, 3356 is an elastomeric material. In one such example, the transparent material is a silicone of a medical grade. In some examples, the silicone may be selected from silicones having a Shore A durometer measurement ranging between 35 and 45; i.e. from soft to medium soft. In further examples, the silicone has a Shore A durometer measurement of between 38 and 42. In one such example, the silicone has a Shore A durometer measurement of 40.

In some examples, a harder durometer measurement may be used to provide the gas delivery tube with greater structural integrity. However, this may also mean that there is greater potential for added pressure should the non-patient contacting side inadvertently come into contact with the face of the patient while wearing the positioning and stabilising structure. This may cause discomfort for the patient.

In other examples, the transparent material may be TPE or TPU of an appropriate softness. An advantage of TPE is its relative low cost and the lower temperatures required for working. For example, TPE can be moulded at temperatures less than 50° C. with a shorter cycle time compared to an elastomer material such as silicone.

In one example, the window sections 3355, 3356 are formed by overmoulding the silicone to strips of textile material, forming the patient contacting side 3351 and non-patient contacting side 3354 respectively. In some examples, the textile material may be laminated or coated to form the gas impermeable layer prior to being cut into strips but in other examples, the strips may be laminated after having been fabricated, for example by flat knitting.

In one example of manufacture, the strips of textile material are inserted into a mould and the window sections 3355, 3356 moulded onto the textile material. This may form a one-piece construction between the textile material and the transparent material. In FIGS. 5 and 6, the window sections 3355, 3356 include semi-circular profiles 3357 on the hollow interior of the gas delivery tube, which may have a complementary shape to the profiles 3357. These may assist in directing the flow of silicone as it is moulded such that it encourages bonding to the textile strips before the portion that forms the window section is filled. This urges the textile strips on either side of the window section towards each other for a more robust bond. Conversely, forming the window section first may bias the textile strips apart, affecting the quality and appearance of the gas delivery tube.

In some examples, a part of the length of the gas delivery tube may be configured with one or more window sections while in other examples, the entire length of the gas delivery tube 3350 may be configured with one or more window sections 3355, 3356. In further examples, the length of the gas delivery tube may be configured with a series of window sections arranged at certain intervals and/or at strategic positions. For example, in certain forms the inferior portion of the gas delivery tube 3350, close to the plenum chamber 3200, is provided with one or more window sections while the superior portion of the gas delivery tube, close to the connection port to the air supply is not. In some of these examples, at least some of the individual window sections may be separated from adjacent window sections by sections of textile material or foam material.

5.3.3.1.4 Transparent Material—Non Patient Contacting Side

In a further example, FIG. 7 shows a gas delivery tube 3350 having a substantially D-shaped profile. The curved portion of the profile is the non-patient contacting side 3354 of the gas delivery tube 3350 and may be formed entirely from a transparent material, while the flat portion of the profile is the patient contacting side 3351 of the gas delivery tube and is comprised entirely of a textile material or foam material. The patient contacting 3351 and non-patient contacting portions 3354 are bonded at their respective flanges which, in use, form the anterior and posterior sides respectively of the gas delivery tube 3350.

In other examples, rather than the D-shaped profile of FIG. 7, the gas delivery tube may have a substantially square or rectangular profile, which may include rounded corners for patient comfort. The rounded corners, as opposed to sharp corners, may assist in reducing potential fault locations (e.g., where gas delivery tube 3350 might fault as a result of repeated pressurization and depressurization).

The arrangement of FIG. 7 and described examples may be advantageous since it will provide a conduit headgear that is comfortable to wear but will also allow the interior of the at least a portion of the gas delivery tube, if not its entire length, to be visible to the patient. The inspection and cleaning of the gas delivery tube may be easier to perform. In other examples, only a portion of the length of the non-patient contacting side may be formed from the transparent material. For example, only the non-patient contacting side of the inferior end of the gas delivery tube may be comprised of the transparent material. In another example, the non-patient contacting side of the superior end of the gas delivery tube may be comprised of the transparent material.

In these examples, the transparent material forming the non-patient contacting side 3354 is an elastomeric material.

In one such example, the transparent material is a silicone of a medical grade. In some examples, the silicone may be selected from silicones having a Shore A durometer measurement ranging between 35 and 45; i.e. from soft to medium soft. In further examples, the silicone has a Shore A durometer measurement of between 38 and 42. In one such example, the silicone has a Shore A durometer measurement of 40.

In other examples, the transparent material may be TPE or TPU of an appropriate softness. The harder the durometer measurement, the greater the potential for added pressure, should the non-patient contacting side 3354 inadvertently come into contact with the face of the patient while wearing the positioning and stabilising structure of the patient interface. This may cause discomfort for the patient.

In this example, for the comfort of the patient, the patient contacting side 3351 of the gas delivery tube 3350 is constructed from an opaque textile material as previously described. In FIG. 7, the textile layer includes an inner layer in the form of a gas impermeable layer 3352 of a laminate of silicone or the like. In some examples, additional layers of adhesive or further laminate layers may be provided. Between the inner gas impermeable layer 3352 and the non-patient contacting side 3354 which, as already described for this example is entirely comprised of an elastomer material and as such is medically compatible with a clean gas flow, the flow path is formed.

Additionally, or alternatively, the patient-contacting side 3351 may be formed from, or may comprise, a foam material. In some examples the tube 3350 may comprise a combination of textile and foam materials. The textile and/or foam materials comprising the patient-contacting side 3351 of the gas delivery tubes may: hold air under pressure, be biocompatible and suitable/approved for use in forming a medical air path, be lighter than silicone tubes, be soft and flexible, generally retain a predetermined shape, be cleanable and be durable for a predetermined lifecycle such as one month, three months, six months, a year or longer.

In some examples, the non-patient contacting side 3354 of the gas delivery tube 3350 may comprise, at least partially, one or more concertina sections 3358, as shown in FIG. 8. Each concertina section 3358 may comprise a portion of the gas delivery tube 3350 having one or more folding portions, pleats, corrugations or bellows as described in PCT Application No. PCT/AU2019/050874, the contents of which are incorporated herein by reference.

In some examples, the concertina section may extend a portion of the length of the non-patient contacting side of the gas delivery tube, as shown in FIG. 8, but in other examples, the concertina section may extend the entire length of the non-patient contacting side of the gas delivery tube. In further examples, the concertina sections 3358 may be located at strategic points along the length of the gas delivery tube. For example, the concertina sections may be located at the points corresponding to the curves of the patient's head (such as the crown and around the jaw, below the line of the mouth), but not at the substantially flat portions of the head (such as the side of the head, between the otobasion superior and otobasion inferior) to assist in the positioning and stabilising structure conforming to the shape of the patient's head.

In other examples, the concertina section may extend partially around the circumference of the non-patient contacting side of the gas delivery tube. In examples, the concertina section may extend to comprise the posterior and anterior sides of the gas delivery tube. In further examples, the concertina section may extend fully around the circumference of the gas delivery tube. In this example, the concertina section may encompass both the patient contacting side and non-patient contacting side of the gas delivery tube. This example may have greater extension functionality, to increase the length of the gas delivery tube, relative to other examples where the concertina section extends only around the circumference, or a portion of the circumference, of the non-patient contacting side.

In the examples of FIGS. 11 and 12, the concertina section 3358 of the gas delivery tube 3350 is comprised at least partially of a textile material or a foam material and at least partially of a transparent material, such as silicone, TPE or TPU as previously described in previous examples. In some examples, the textile material or foam material may be provided solely to the patient contacting side of the gas delivery tube, leaving the non-patient contacting side comprised partially or entirely of transparent material. The textile material and the transparent material may have similar stretch characteristics so that the patient and non-patient sides are able to stretch together (e.g., the concertina does not curve while stretching). However, in the example of FIGS. 11 and 12, the non-patient contacting side includes an elongate strip of textile material in the form of a textile pad 3308 running the length of the gas delivery tube. In this example, the gas delivery tube 3350 is comprised entirely of transparent material and the textile pad 3308 has been bonded (e.g., via overmolding, an adhesive, etc.) to the non-patient contacting side of the gas delivery tube 3350. In other words, the textile material in this example does not contact the pressurized air as it flows through the gas delivery tube 3350.

In some further examples, the concertina section is provided to both the non-patient contacting side and the patient contacting side. In this example, the concertina section of the patient contacting side may also be comprised of a textile material or foam material for patient comfort.

The use of a gas delivery tube 3350 having one or more concertina sections confers the gas delivery tube 3350 with some lengthening and bending functionality, which may be advantageous in providing conduit headgear that is able to better conform to the shape of the patient's head. In FIG. 10 for example, the superior portions of the gas delivery tubes 3350 of the positioning and stabilising structure 3300 are provided with a concertina section 3358. This is advantageous as it may allow the gas delivery tube to have some extensionability and/or bendability to conform to the upper portion of the patient's head.

As seen in FIG. 8, the concertina sections 3358 may be comprised of a series of external ridges 3359A and grooves 3359B alternatingly formed along at least a portion of the non-patient contacting side 3354 of the gas delivery tube 3350. In some examples, corresponding ridges and grooves may be provided to the interior of the gas delivery tube but this may compromise the cost efficiency of manufacture.

In some examples, the alternating ridges 3359A and grooves 3359B may function like folds or bellows able to fold and unfold independently or in concert to shorten or lengthen the concertina section 3358 and hence the respective gas delivery tube 3350. A large groove depth (or ridge height) may provide for a more extendable or bendable tube 3350. When tension is applied to the tubes 3350, the ridges 3359A and grooves 3359B of the extendable concertina section 3358 may be pulled away from each other which straightens out the tube wall, lengthening the tubes 3350. In this example, the concertina section 3358 is biased to an original (e.g. unextended) length. Upon release of headgear tension the ridges 3359A and grooves 3359B are biased back to an original configuration in which the concertina section 3358 and the tubes 3350 have original lengths. This may assist in the gas delivery tube conforming to the shape of the patient's head. The stretching or extending of the concertina section on the gas delivery tube 3350 may be substantially elastic, so that it provides a similar force to the plenum chamber 3200 which each successive use.

In other examples, the alternating ridges 3359A and grooves 3359B of the concertina section may be formed as corrugations such that the gas delivery tube is able to deform and bend. In this example, the concertina section may only have limited or no functionality to be shortened or lengthened. The ridges 3359A and grooves 3359B may facilitate a change in shape of the concertina section 3358 of the gas delivery tube 3350 which assists in helping the gas delivery tube conform to the patient's head.

5.3.3.1.5 Rigidity

In some examples of the present technology, the gas delivery tubes 3350, or portions of the gas delivery tubes, of the positioning and stabilising structure 3300 may be configured to be more resistant to bending in or about some directions or axes than in or about others. A tube 3350 that comprises relatively rigid portions on both the anterior and posterior sides of the tube 3350 may advantageously have a higher resistance to bending towards both the anterior and posterior sides of the tube 3350 when in use. However, in some examples a rigid portion is provided to only one of the anterior or posterior sides of the tube 3350 since, depending on the rigidity, a rigid portion on one side only may provide a sufficient resistance to bending towards both directions. In other examples, a rigid portion may be provided along the entire length of the gas delivery tube 3350 while in further examples, a rigid portion is provided to only a portion of the length of the gas delivery tube 3350. For example, the rigid portion may be provided to one of the inferior portions or superior portions of the tube. For example, a superior portion of each tube 3350 of the positioning and stabilising structures 3300 shown in FIGS. 3 and 4 may be more bendable in a particular direction in comparison to an orthogonal direction. For example, having the superior portion of the gas delivery tube more bendable may assist in the positioning and stabilising structure conforming to the shape of the patient's skull, particularly around the curvature of the crown.

Each gas delivery tube 3350 of the positioning and stabilising structure 3300 may comprise a superior tube portion 3304 in use extending, for example, posteriorly from the top of the patient's head to around the line of the otobasion superior, and configured to overlie a superior region of the patient's head in use. Conversely, an inferior portion 3306 of each tube 3350 of the positioning and stabilising structures 3300 shown in FIGS. 3 and 4, the inferior portion in use extending posteriorly from the otobasion superior of the patient's head, may be more bendable in a particular direction in comparison to an orthogonal direction.

In some examples of the present technology, the superior tube portion 3304 may also comprise one or more stiffened portions relative to the inferior tube portion 3306. The stiffened portion(s) may be configured to provide a higher resistance to relative movement in an anterior and/or posterior direction than in a superior and/or inferior direction. This may be advantageous when dealing with, for example, any drag arising from the air circuit. The stiffened portions may, in some examples, be provided to the entire length of the tube 3350, and in some examples may provide varying stiffnesses along the length of the tube 3350.

In examples, the stiffened portion(s) of the gas delivery tube may be provided by the window sections. Being formed from an elastomeric material, the window sections may inherently have greater rigidity than the textile material or foam material forming at least a substantial portion of the remainder of the gas delivery tube.

In some examples, the relative rigidity of the gas delivery tube may be determined by the configuration of the window sections. In the embodiment of FIG. 5 for example, the rigidity of the gas delivery tube 3350 may be enhanced through increasing the thickness of one or both of the window sections 3355, 3356. In another example, the rigidity of the gas delivery tube may be enhanced through decreasing the thickness of one of the window sections 3355 relative to the other window section 3356. Depending on the desired rigidity, the thickness of the window section(s) may increase or decrease along the length of the gas delivery tube 3350. This may give differing rigidities to the inferior tube portion 3306 and superior tube portion 3304 of the gas delivery tube.

A similar increase in rigidity of the gas delivery tube may be achieved by increasing the relative width of one or both of the window sections 3355, 3356, i.e. reducing the amount of textile material present and increasing the amount of the silicone present in the window section, i.e. increasing the ratio of surface area of the window section relative to the textile material of the non-patient contacting side of the gas delivery tube. The ratio of window section relative to textile material may range from 1:10 to 1:1. For example, in FIG. 5, the window sections 3355, 3356 are about an eighth of the width of the textile strip forming the non-patient contacting side 3354, i.e. a ratio of 1:8. Doubling the width of the window sections 3355, 3356 with a corresponding decrease in width of the textile material forming the non-patient contacting side 3354 may increase the rigidity of the gas delivery tube. The width of the window sections may increase or decrease along the length of the gas delivery tube 3350, providing differing rigidities to the inferior 3306 and superior portions 3304 of the gas delivery tube.

The rigidity may also increase the rigidity of the gas delivery tube 3350 by adding (e.g., sewing) rigidized threads to the textile material. The rigidized threads may provide a stiffness to the textile material, without substantially increasing the weight of the textile material. The rigidized threads could be used instead of a window section with an increased width, in order to reduce weight, and improve patient compliance.

In embodiments where the window sections 3355, 3356 are positioned along the posterior and anterior sides of the gas delivery tube (such as in FIGS. 5 and 6), one or the other of the window sections may be configured to be more rigid than the other. For example, the window section of the anterior side of the gas delivery tube may be configured such that it is more rigid that the window section of the posterior side of the gas delivery tube. This may mean that the gas delivery tube 3350 is more resistant to forces applied from a posterior direction (such as may occur when the air circuit drags or catches on bedding or the like). In another example, the window section of the posterior side of the gas delivery tube may be configured such that it is more rigid that the window section of the anterior side of the gas delivery tube. This may mean that the gas delivery tube 3350 is more resistant to forces applied from an anterior direction.

5.3.3.1.6 Alternative Gas Delivery Tube Construction

In another example of the present technology, FIG. 9 shows the inferior portion 3306 of a gas delivery tube 3350 when it has be decoupled from the plenum chamber 3200. In contrast to previous examples described, both the patient contacting side 3351 and non-patient contacting side 3354 of the gas delivery tube 3350 is constructed primarily from a transparent material in the form of an elastomer. This means that the flow path within the gas delivery tube 3350 (or a substantial part thereof) is defined entirely by the elastomer. In examples, the elastomer is a silicone, which is gas impermeable and medically suitable for use for defining a hygienic flow path. Other examples of elastomers may be TPE or TPU.

The patient contacting side 3351 is configured to permanently or temporarily receive a textile pad 3308 which provides a comfortable, softer surface that, in use, contacts the patient's face. In other words, the textile pad 3308 does not form a portion of the passage through which pressurized air flows. In examples, the textile pad 3308 may be added during manufacture or alternatively provided separately to the gas delivery tubes for the patient to secure to the gas delivery tube if desired. This may allow for the provision of conduit headgear in a non-textile form, leaving the patient to place the textile pads on certain areas of the patient contacting side of the gas delivery tube, according to their preference. For example, textile pads may be applied to the superior portion of the gas delivery tube 3350, which contacts the crown of the head of the patient.

As the textile pad 3308 does not need to be configured with a surface that forms part of the flow path of the gas delivery tube 3350, this function being fulfilled entirely by the transparent material forming at least a substantial part of the flow path within the gas delivery tube, there may be no need for a textile that incorporates a gas impermeable layer. The textile pad 3308 may be comprised of one or more fabrics, for example, nylon, polyester, or spandex or blends of these. In some examples, the textile pad 3308 may be comprised of a sufficiently stretchable and elastic material such that it does not inhibit the bendability of the conduit headgear, for example, to allow for ready movement of the concertina sections 3358 of the conduit headgear of FIGS. 10 to 12.

In these examples, the textile pad 3308 is bonded to the transparent material through the use of an adhesive or similar bonding agent. In other examples, the textile pad 3308 may be secured, for example, by hook and loop material such as VELCRO™, to the transparent material. In further examples, the transparent material may be over-moulded to the textile pad 3308.

In some examples, to assist with locating the textile pad 3308, the patient contacting side 3351 of the gas delivery tube 3350 may be moulded or otherwise formed to comprise a partial recess or depression. This may be advantageous in providing a highly integrated look and feel to the gas delivery tube 3350, which may make it more appealing to the consumer. In some examples, the recess may be provided with one of a hook and loop material, with a reverse side of the textile pad 3308 provided with the other of the hook and loop material. This allows the textile pads to be removed for washing to remove skin oils and dirt arising from contact with the patient's face.

In FIG. 9 the textile pad 3308 extends from the inferior end of the gas delivery tube 3350 as far in the superior direction as the tab 3312 extending posteriorly from the gas delivery tube. In some examples, the textile pad 3308 may be configured with a corresponding tab such that this covers the tab 3312 of the gas delivery tube 3350. This may improve comfort in the event that the tab 3312 of the gas delivery tube comes into contact with the face and/or hair of the patient while the positioning and stabilising structure is worn.

FIG. 9 shows only the inferior portion 3306 of the gas delivery tube being provided with a textile pad 3308, but in other examples, the superior portion 3304 of the gas delivery tube 3350 may also or alternatively be configured with a textile pad 3308. This may be a separate textile pad to that provided to the inferior portion 3306 of the gas delivery tube or, as shown in FIG. 10, a single textile pad may cover both the superior 3304 and inferior 3306 portions of the gas delivery tube 3350. A textile material covering both superior 3304 and inferior 3306 portions may be particularly beneficial for patients with little or no hair on the scalp or sides of the head and who dislike the contact of elastomeric material against the skin. There is also little risk of the elastomeric material gripping and pulling at the patient's hair should the positioning and stabilising structure inadvertently move on the patient's head.

In some examples, such as that of FIGS. 11 and 12, where the patient contacting side of the gas delivery tube 3350 comprises a textile pad 3308, a textile pad may also be applied to the non-patient contacting side of the gas delivery tube 3350 leaving the window sections 3355, 3356 uncovered. In this example, the transparent material forms at least a substantial part of the flow path within the gas delivery tube. The use of a textile pad 3308, bonded through the use of adhesive, moulding techniques or hook and loop material such as VELCRO™, may provide a finish to the non-patient contacting side of the gas delivery tube that is aesthetically pleasing and comfortable to touch should the patient need to do so (for example, when donning and doffing the positioning and stabilising structure.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., an elbow swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Anti-Asphyxia Valve

In one form, the patient interface 3000 includes an anti-asphyxia valve.

5.3.8 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

5 GLOSSARY

For the purposes of the present technology disclosure, in certain forms of the present technology, one or more of the following definitions may apply. In other forms of the present technology, alternative definitions may apply.

5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water (H$_2$O) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including cmH$_2$O, g-f/cm$^2$ and hectopascal. 1 cmH$_2$O is equal to 1 g-f/cm$^2$ and is approximately 0.98 hectopascal. In this specification, unless otherwise stated, pressure is given in units of cmH$_2$O.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.1.1.1 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure. 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.1.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Expiratory portion of a breathing cycle: The period from the start of expiratory flow to the start of inspiratory flow.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.1.3 Anatomy
5.1.3.1 Anatomy of the Face

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lip, lower (labrale inferius): A point on the face between the mouth and supramenton, lying in the median sagittal plane.

Lip, upper (labrale superius): A point on the face between the mouth and nose, lying in the median sagittal plane.

Nares (Nostrils): Approximately ellipsoidal apertures forming the entrance to the nasal cavity. The singular form of nares is naris (nostril). The nares are separated by the nasal septum.

Otobasion inferior: The lowest point of attachment of the auricle to the skin of the face.

Otobasion superior: The highest point of attachment of the auricle to the skin of the face.

5.1.3.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.1.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.1.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear. Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.1.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. The outward normal vector at p points away from the surface. In some examples we describe the surface from the point of view of an imaginary small person standing upright on the surface.

5.1.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). Such curves are often referred to as concave.

Zero curvature: If the curve at p is a straight line, the curvature will be taken to be zero (if the imaginary small person leaves the point p, they can walk on a level, neither up nor down).

Negative curvature: If the curve at p turns away from the outward normal, the curvature in that direction at that point will be taken to be negative (if the imaginary small person leaves the point p they must walk downhill). Such curves are often referred to as convex.

5.1.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small.

Principal curvatures and directions: The directions of the normal planes where the curvature of the curve takes its maximum and minimum values are called the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.1.5.3 Holes

A surface may have a one-dimensional hole, e.g. a hole bounded by a plane curve or by a space curve. Thin structures (e.g. a membrane) with a hole, may be described as having a one-dimensional hole.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit.

5.2 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means+/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.3 REFERENCE SIGNS LIST | |
|---|---|
| 1000 | Patient |
| 1100 | Bed partner |
| 3000 | Patient interface |
| 3100 | Sealing or seal-forming structure |
| 3150 | Cushion module |
| 3200 | Plenum chamber |
| 3300 | Positioning and stabilising structure/headgear |
| 3304 | Superior tube portion |
| 3306 | Inferior tube portion |
| 3308 | Textile pad |
| 3310 | Strap |
| 3312 | Tab (for strap) |
| 3350 | Headgear tubes |
| 3351 | Patient contacting side (of headgear tube) |
| 3352 | Inner gas-impermable layer |
| 3353 | Outer textile layer |
| 3354 | Non-patient contacting side (of headgear tube) |
| 3355 | Window section (anterior side) |
| 3356 | Window section (posterior side) |
| 3357 | Semi-circular profiles (of window sections) |
| 3358 | Concertina section (of headgear tube) |
| 3359A | Ridges (of concertina section) |
| 3359B | Grooves (of concertina section) |
| 3360 | Crown Connector |
| 3390 | Fluid connection opening |
| 3400 | Vent |
| 3600 | Connection port |
| 3610 | Elbow |
| 4000 | RPT device |
| 4170 | Air circuit |
| LA | Longitudinal axis |
| TA | Transverse axis |
| θ | Angle |

The invention claimed is:

1. A patient interface comprising:
  a seal-forming structure constructed and arranged to form a seal with a region of the patient's face surrounding an entrance to the patient's airways for sealed delivery of a flow of pressurized air at a therapeutic pressure of at least 6 cmH$_2$O above ambient air pressure throughout the patient's respiratory cycle in use;
  a plenum chamber pressurisable to the therapeutic pressure of at least 6 cmH2O above ambient air pressure; and
  positioning and stabilising structure to provide a force to hold the seal-forming structure in a therapeutically effective position on a patient's head, the positioning and stabilising structure comprising:
    at least one gas delivery tube coupled to the plenum chamber and configured to receive the flow of pressurized air from a connection port on top of the patient's head and to deliver the flow of pressurized air to the entrance of the patient's airways via the plenum chamber, the at least one gas delivery tube being constructed and arranged to contact, in use, at least a region of the patient's head superior to an otobasion superior of the patient's head, the at least one gas delivery tube comprising a tube wall having an interior passage for flow of pressurized air along a longitudinal axis of the tube to the seal-forming structure, wherein at least a portion of the tube wall comprises:
      a patient contacting portion comprising a layer of textile material or foam material configured to lie against the patient's head in use; and
      a non-patient contacting portion, wherein at least a section of the non-patient contacting portion is comprised of a transparent and/or translucent material positioned and configured to allow viewing of the interior passage from outside;
    wherein the layer of textile material or foam material is bonded to the transparent and/or translucent material so that the tube wall is formed as a one piece construction;
    wherein a plane extending generally transverse to the longitudinal axis contains both (1) the layer of textile material or foam material and (2) the transparent and/or translucent material, so that the patient may view the interior passage along a transverse axis extending through the plane; and
  wherein a portion of the section of the non-patient contacting portion comprising transparent and/or translucent material is configured as a rigidising element; and
  wherein the at least one gas delivery tube further comprises an anterior side positioned between the patient contacting portion and the non-patient contacting portion, a posterior side positioned between the patient contacting portion and the non-patient contacting portion, and each of the anterior side and the posterior side includes transparent and/or translucent material and at least one semi-circular profile facing the interior passage.

2. The patient interface of claim 1, wherein the patient contacting portion comprises an outer layer of textile material or foam material configured to lie against the patient's head in use, and at least a first inner layer of a thermoplastic material forming at least a portion of an air path within the at least one gas delivery tube, the first inner layer being bonded to the outer layer.

3. The patient interface of claim 1, wherein the patient contacting portion comprises a single layer of textile material or foam material, and wherein the single layer of textile material or the foam material is impermeable.

4. The patient interface according to claim 1, wherein the patient contacting portion comprises a single layer of textile material or foam material, and wherein the single layer of textile material or foam material is coated with an impermeable substance along at least one surface, which forms an inner surface of the at least one gas delivery tube configured to be contacted by the flow of pressurized air.

5. The patient interface of claim 1, wherein the patient contacting portion comprises a single layer of textile material or foam material, wherein the single layer of textile material or foam material comprises a blend of polyamide, wherein the single layer of textile material or foam material comprises a nylon, polyester and/or spandex, and wherein the single layer of textile material or foam material also comprises one or more laminate coats of silicone.

6. The patient interface of claim 1, wherein the patient contacting portion comprises a single layer of textile material or foam material, wherein the non-patient contacting portion comprises a section configured to receive the section of transparent and/or translucent material, and wherein the section of transparent material includes an adhesive layer configured to be bonded to the single layer of textile material or foam material.

7. The patient interface of claim 1, wherein one of the patient contacting portion or non-patient contacting portion is configured to receive an adhesive layer to which the other of the patient contacting portion or non-patient contacting portion is bonded.

8. The patient interface of claim 1, wherein the non-patient contacting portion comprises an outer layer of transparent material and at least a first inner layer of a thermoplastic material defining at least a portion of an air path within the at least one gas delivery tube.

9. The patient interface of claim 1, wherein a portion of the section of the non-patient contacting portion comprising the transparent and/or translucent material comprises a concertina section, and wherein a textile material or a foam material is overmolded onto the concertina section, wherein the textile material or the foam material is on the patient contacting portion, and configured to contact the patient, and/or wherein the textile material or the foam material is on the non-patient contacting portion.

10. The patient interface of claim 1, wherein a portion of the section of the non-patient contacting portion comprising transparent and/or translucent material comprises a series of corrugations.

11. The patient interface of claim 1, wherein the section of the non-patient contacting portion comprising transparent and/or translucent material runs substantially along a length of the at least one gas delivery tube.

12. The patient interface of claim 1, wherein the section of the non-patient contacting portion comprising transparent and/or translucent material is arranged in discrete sections, each section separated by a section of non-transparent material and/or non-translucent material, and wherein the section of non-transparent material and/or translucent material is a textile material or a foam material.

13. The patient interface of claim 1, wherein the non-patient contacting portion includes an anterior facing side and a posterior facing side, configured to face in an anterior direction and a posterior direction respectively, in use, wherein the anterior facing side and the posterior facing side are each constructed from the transparent and/or translucent material, and wherein the transverse axis extends generally from the anterior direction to the posterior direction includes only the transparent and/or translucent material.

14. The patient interface of claim 1, wherein the section of the non-patient contacting portion comprising transparent and/or translucent material is formed from an elastomer that is one or more of a) silicone; b) thermoplastic elastomer; or c) thermoplastic polyurethane.

15. The patient interface of claim 1, wherein the at least one gas delivery tube comprises a substantially rectangular cross section with two or more rounded corners.

16. The patient interface of claim 1, wherein the at least one gas delivery tube has a width ranging from 34 mm to 18 mm along a length of the at least one gas delivery tube, and wherein the at least one gas delivery tube has a height ranging from 8 mm to 6 mm along a length of the at least one gas delivery tube.

17. The patient interface of claim 1, wherein the non-patient contacting portion comprises a transparent material only.

18. The patient interface of claim 1, wherein the at least one gas delivery tube is selectively coupled to the plenum chamber, and is configured to be removed in order to allow the patient to clean within the tube.

19. The patient interface of claim 1, wherein the rigidising element is provided along the entire length of the at least one gas delivery tube and is configured to rigidize the entire tube.

20. The patient interface of claim 1, wherein the rigidising element includes a higher resistance to bending in a first direction than in a second direction, the first direction being generally orthogonal to the second direction, and wherein, in use, the first direction is an anterior-posterior direction and the second direction is an orthogonal direction, the at least one gas delivery tube configured to bend in the orthogonal direction in order to conform to the shape of the patient's skull.

21. The patient interface of claim 1, wherein the at least one gas delivery tube comprises a substantially D-shaped cross section, and wherein the substantially D-shaped cross section includes a substantially flat surface and an arcuate surface, the substantially flat surface forming the patient contacting portion and the arcuate surface forming the non-patient contacting portion.

22. The patient interface of claim 21, wherein the arcuate surface includes a first section and a second section, the first section being constructed from the transparent and/or translucent material, and the second section being constructed from the textile material or foam material, and wherein the first section is directly coupled to the substantially flat surface, and the second section is disposed opposite to the substantially flat surface.

23. The patient interface of claim 1, wherein the patient contacting portion and the non-patient contacting portion each respectively comprise a side that in use faces anteriorly and a side that in use faces posteriorly, and wherein the respective anterior and posterior sides of the patient contacting portion and the non-patient contacting portion are joined along a length of the at least one gas delivery tube, and wherein at least one or both of the anterior side and posterior side of the non-patient contacting side comprises the transparent and/or translucent material.

24. The patient interface of claim 23, wherein the anterior side of the non-patient contacting portion comprises a greater rigidity than the posterior side of the non-patient contacting portion.

25. The patient interface of claim 24, wherein a thickness of the section of the non-patient contacting portion comprising transparent and/or translucent material is greater at a first portion of the at least one gas delivery tube relative to a second portion of the at least one gas delivery tube, and wherein a width of the section of the non-patient contacting portion comprising transparent and/or translucent material is greater at a first portion of the at least one gas delivery tube relative to a second portion of the at least one gas delivery tube.

26. The patient interface of claim 23, wherein the anterior side of the non-patient contacting portion and/or the posterior side of the non-patient contacting portion has a rigidity which varies along a length of the at least one gas delivery tube.

27. The patient interface of claim 26, wherein a superior portion of the at least one gas delivery tube proximate to the connection port has a greater resistance to relative movement than an inferior portion of the tube proximate to the plenum chamber, the greater resistance to relative movement in the superior portion is configured to limit drag from an air circuit configured to connect to the connection port.

28. The patient interface of claim 23, wherein a rigidity of the anterior side of the non-patient contacting portion and/or the posterior side of the non-patient contacting portion is greater at an inferior portion of the at least one gas delivery tube than at a superior portion of the at least one gas delivery tube.

29. A method of manufacturing the patient interface of claim 1, the method comprising:
    positioning the layer of textile material or foam material in a mold;
    introducing the transparent and/or translucent material into the mold;
    bonding the transparent and/or translucent material to the layer of textile material and/or foam material in order to form the at least one gas delivery tube; and
    connecting the at least one gas delivery tube to the plenum chamber and/or the seal forming structure.

30. The method of claim 29, wherein the mold includes a semi-circular protrusion and the transparent and/or translucent material flowing around the semi-circular protrusion and creating the at least one semi-circular profile, and wherein the semi-circular protrusion directs the transparent and/or translucent material toward the layer of textile material or foam material in order to allow bonding between the transparent and/or translucent material and the layer of textile material or foam material prior to forming the non-patient contacting portion.

* * * * *